(12) United States Patent
Zhang et al.

(10) Patent No.: US 9,187,772 B2
(45) Date of Patent: *Nov. 17, 2015

(54) **L-MALATE PRODUCTION BY METABOLICALLY ENGINEERED *ESCHERICHIA COLI***

(75) Inventors: Xueli Zhang, Tianjin (CN); Xuan Wang, Gainesville, FL (US); Keelnatham T. Shanmugam, Gainesville, FL (US); Lonnie O'Neal Ingram, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/819,773

(22) PCT Filed: Sep. 1, 2011

(86) PCT No.: PCT/US2011/050146
§ 371 (c)(1),
(2), (4) Date: Feb. 28, 2013

(87) PCT Pub. No.: WO2012/031079
PCT Pub. Date: Mar. 8, 2012

(65) Prior Publication Data
US 2013/0157330 A1 Jun. 20, 2013

Related U.S. Application Data

(60) Provisional application No. 61/379,077, filed on Sep. 1, 2010.

(51) Int. Cl.
*C12P 7/46* (2006.01)
*C12N 1/20* (2006.01)
(Continued)

(52) U.S. Cl.
CPC ... *C12P 7/46* (2013.01); *C12N 1/20* (2013.01); *C12N 9/001* (2013.01); *C12N 9/88* (2013.01); *C12P 7/42* (2013.01); *C12Y 103/01006* (2013.01); *C12Y 401/01031* (2013.01)

(58) Field of Classification Search
None
See application file for complete search history.

(56) References Cited

U.S. PATENT DOCUMENTS

2010/0009419 A1  1/2010  Burk et al.
2010/0184171 A1  7/2010  Jantama et al.
(Continued)

FOREIGN PATENT DOCUMENTS

EP         2220233 B1 *  4/2012
WO    WO 2008115958 A2 *  9/2008
(Continued)

OTHER PUBLICATIONS

Yoshida et al "Enhanced hydrogen production from glucose using ldh- and frd-inactivated *Escherichia coli* strains", Appl. Microbiol. Biotechnol., vol. 73, pp. 67-72, 2006.*
(Continued)

*Primary Examiner* — Robert Mondesi
*Assistant Examiner* — Richard Ekstrom
(74) *Attorney, Agent, or Firm* — Saliwanchik, Lloyd & Eisenschenk

(57) ABSTRACT

A process for the production of malic acid in commercially significant quantities from the carbon compounds by genetically modified bacterial strains (GMBS; also referred to as biocatalysts or genetically modified microorganisms) is disclosed. Microorganisms suitable for the production of malic acid can be cultured in one or two-step processes as disclosed herein.

11 Claims, 2 Drawing Sheets

(51) Int. Cl.
C12N 9/02 (2006.01)
C12N 9/88 (2006.01)
C12P 7/42 (2006.01)

(56) References Cited

U.S. PATENT DOCUMENTS

2011/0039327 A1* 2/2011 Winkler et al. .......... 435/254.21
2012/0058530 A1* 3/2012 Zhang et al. .................. 435/145

FOREIGN PATENT DOCUMENTS

WO  WO 2010059616 A2 * 5/2010
WO  WO 2010111344 A2 * 9/2010

OTHER PUBLICATIONS

Jojima et al., "Sugar transporters in efficient utilization of mixed sugar substrates: current knowledge and outlook", Appl. Microbiol. Biotechnol., vol. 85, pp. 471-480, 2010.*
Cao et al., "Metabolically engineered *Escherichia coli* for biotechnological production of four-carbon 1,4-dicarboxylic acids", Journal of Industrial Microbiology and Biotechnology, vol. 38, pp. 649-656, 2011.*
Zhang, X. et al. "Fermentation of Glycerol to Succinate by Metabolically Engineered Strains of *Escherichia coli*" *Applied and Environmental Microbiology*, Apr. 2010, pp. 2397-2401, vol. 76, No. 8.
Zhang, X. et al. "L-Malate Production by Metabolically Engineered *Escherichia coli*" *Applied and Environmental Microbiology*, Jan. 2011, pp. 427-434, vol. 77, No. 2.
Causey, T. B. "Engineering *Escherichia coli* for efficient conversion of glucose to pyruvate" *Proc Natl Aced Sci USA*, Feb. 24, 2004, pp. 2235-2240, vol. 101, No. 8.
Causey, T. B. "Engineering the metabolism of *Escherichia coli* W3110 for the conversion of sugar to redox-neutral and oxidized products: homoacetate production" *Proc Natl Acad Sci USA*, Feb. 4, 2003, pp. 825-832, vol. 100, No. 3.
Grabar, T. B. "Methylglyoxal bypass identified as source of chiral contamination in $_L$(+) and $_D$(−)-lactate fermentations by recombinant *Escherichia coli*" *Biotechnol Lett*, 2006, pp. 1527-1535, vol. 28.
Henry, C. S. "Genome-scale thermodynamic analysis of *Escherichia coli* metabolism" *Biophys J*, Feb. 2006, pp. 1453-1461, vol. 90.

Jantama, K. "Combining metabolic engineering and metabolic evolution to develop nonrecombinant strains of *Escherichia coli* C that produce succinate and malate" *Biotechnol Bioeng*, Apr. 1, 2008, pp. 1140-1153, vol. 99, No. 5.
Jantama, K. "Eliminating side products and increasing succinate yields in engineered strains of *Escherichia coli* C" *Biotechnol Bioeng*, Dec. 1, 2008, pp. 881-893, vol. 101, No. 5.
Kao, K. C. "A global regulatory role of gluconeogenic genes in *Escherichia coli* revealed by transcriptome network analysis" *J Biol Chem*, Oct. 28, 2005, pp. 36079-36087, vol. 280, No. 43.
Karp, P. D. "Multidimensional annotation of the *Escherichia coli* K-12 genome" *Nucleic Acids Res*, 2007, pp. 7577-7590, vol. 35, No. 22.
Moon, S. Y. "Metabolic engineering of *Escherichia coli* for the production of malic acid" *Biochem Eng J*, 2008, pp. 312-320, vol. 40.
Peleg, Y., "A simple plate-assay for the screening of L-malic acid producing microorganisms" *FEMS Microbiol Lett*, 1990, pp. 233-236, vol. 67, No. 3.
Roa Engel, C. A. "Fumaric acid production by fermentation" *Appl Microbiol Biotechnol*, 2008, pp. 379-389, vol. 78.
Stols, L. "Production of succinic acid through overexpression of $NAD^+$—dependent malic enzyme in an *Escherichia coli* mutant" *Appl Environ Microbiol*, Jul. 1997, pp. 2695-2701, vol. 63, No. 7.
Tseng, C.-P. "Oxygen—and growth rate-dependent regulation of *Escherichia coli* fumarase (FumA, FumB, and FumC) activity" *J Bacteriol*, Jan. 2001, pp. 461-467, vol. 183, No. 2.
Zelle, R. M. "Malic acid production by *Saccharomyces cerevisiae*: engineering of pyruvate carboxylation, oxaloacetate reduction, and malate export" *Appl Environ Microbiol*, May 2008, 2766-2777, vol. 74, No. 9.
Zhang, X. "Metabolic evolution of energy-conserving pathways for succinate production in *Escherichia coil*" *Proc Natl Acad Sci USA*, 2009, pp. 20180-20185, vol. 106, No. 48.
Zhang, X. "Production of L-alanine by metabolically engineered *Escherichia coli*" *Appl Microbiol Biotechnol*, 2007, pp. 355-366, vol. 77.
Zhang, X. "Reengineering *Escherichia coli* for Succinate Production in Mineral Salts Medium" *Appl Environ Microbiol*, 2009, pp. 7807-7813. vol. 75, No. 24.
Written Opinion in International Application No. PCT/US2011/050146, Jun. 26, 2012, pp. 1-7.

* cited by examiner

L-MALATE PRODUCTION BY METABOLICALLY ENGINEERED *ESCHERICHIA COLI*

CROSS-REFERENCE TO RELATED APPLICATION

This application is the U.S. national stage application of International Patent Application No. PCT/US2011/050146, filed Sep. 1, 2011, which claims the benefit of U.S. Provisional Application Ser. No. 61/379,077, filed Sep. 1, 2010, the disclosures of which are hereby incorporated by reference in their entirety, including all figures, tables and amino acid or nucleic acid sequences.

This invention was made with government support under U.S. Department of Energy Grant No. DE-FG36-08-GO88142). The government has certain rights in the invention.

BACKGROUND OF THE INVENTION

The U.S. Department of Energy has identified malic acid and other 1,4-dicarboxylic acids (fumaric and succinic) as building block chemicals that could be made in large quantities from renewable carbohydrates and converted to high volume products (27). Presently, malic acid usage is limited to pharmaceuticals, cosmetics, and acidulants in the food industry (2, 23). It is produced as a racemic mixture by chemical synthesis (hydration of maleic or fumaric acid) or as enantiomerically pure L-malate by the enzymatic hydration of fumarate (immobilized cells or fumarase) (2, 6, 21). Substrates for the synthesis of malic acid (maleic acid, fumaric acids, maleic anhydride) are derived from petroleum (22). Increases in oil and gas prices coupled with concerns about climate change and global warming have renewed interests in the production of malic acid by microbial fermentation (7).

Malate can be made by a wide range of microorganisms using aerobic or microaerophilic processes (Table 1) (1, 16, 18-19, 25). *Aspergillus flavus* is the best known producer (1). This organism can ferment glucose to malate at relatively high yield (1.28 mol malate per mol glucose), titer (113 g liter$^{-1}$) and productivity (0.59 g liter$^{-1}$ h$^{-1}$). However, this biocatalyst is not useful in industrial processes due to the potential for aflatoxin production (1, 5). A sugar-tolerant yeast, *Zygosaccharomyces rouxii*, was recently found to produce 75 g liter$^{-1}$ malic acid when cultured aerobically in complex medium containing 300 g liter$^{-1}$ glucose (25). Malate has also been produced by engineered strains of *Saccharomyces cerevisiae* (20, 28). Overexpression of plasmid-born genes encoding pyruvate carboxylase, cytosolic malate dehydrogenase, and a heterologous malate transporter resulted in the production of 59 g liter$^{-1}$ malate (28).

*Escherichia coli* has been previously engineered in our lab for the efficient production of succinate by increasing the expression of pyruvate carboxykinase, an energy-conserving reaction (12-13, 29, 31). Malate is an intermediate in this process (FIG. 1A) but requires only a single reducing equivalent for synthesis from phosphoenolpyruvate (PEP). A homo-malate fermentation could produce 2 moles of malate per mole of glucose at redox balance, preserve all glucose carbon, and incorporate two additional molecules of $CO_2$ with a product yield of 149% that of glucose (weight basis). Thus, a need exists for providing genetically engineered microorganisms suitable for the production of malate.

BRIEF SUMMARY OF THE INVENTION

A process for the production of malic acid in commercially significant quantities from the carbon compounds by genetically modified bacterial strains (GMBS; also referred to as biocatalysts or genetically modified microorganisms) is disclosed. Microorganisms suitable for the production of malic acid can be cultured in one or two-step processes as disclosed herein.

BRIEF DESCRIPTION OF THE DRAWINGS

FIG. 1A. Central pathway for succinate production in KJ060 and KJ073 showing the inactivation of fumarase genes predicted to accumulate malate. FIG. 1B. Malate pathway in XZ658 with gene deletions listed.

DETAILED DISCLOSURE OF THE INVENTION

Figure 1:
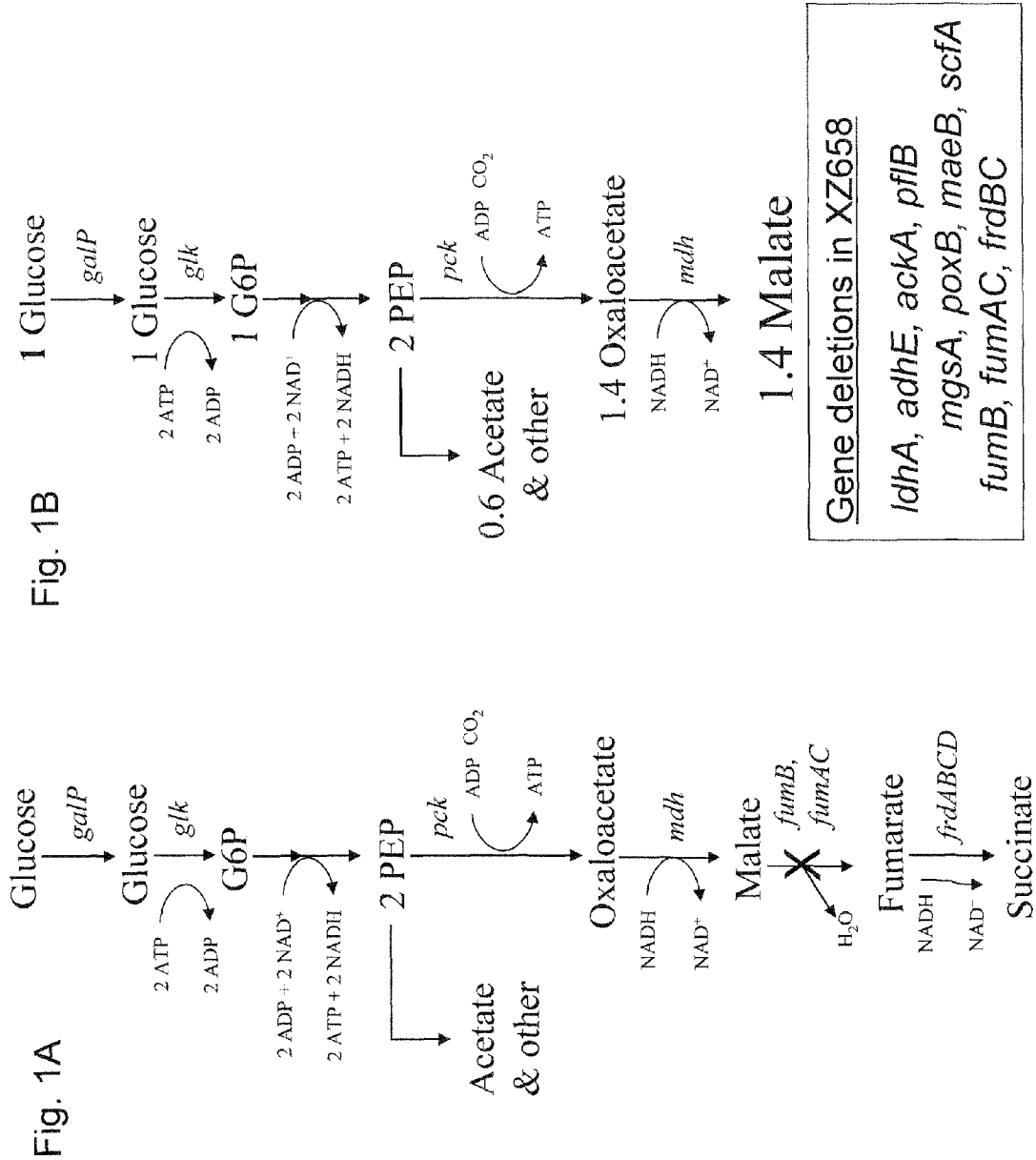
FIGS. 1A-1B. Engineering a pathway for malate production.

It is an objective to provide a method for obtaining a biocatalyst (a genetically modified microorganism) for manufacturing malic acid (malate). Methods for producing the biocatalysts utilize genetic manipulations, and, optionally, the process of metabolic evolution.

In one aspect, the mutation of the genes in the chromosome of the microorganism is accomplished without introducing any exogenous genetic material. Another aspect provides for the mutation of endogenous genes by the introduction of one or more point mutation(s) or by introducing a stop codon in the open reading frame of the endogenous gene that is being modified. In another aspect, the open reading frame of the endogenous gene can be deleted from the chromosomal DNA.

In certain aspects, an exogenous nucleotide sequence may be introduced to inactivate a target gene for the purpose of selecting a bacterial strain with a mutated gene having a desired phenotype. The exogenous nucleotide sequence introduced into the microbial genome can be subsequently removed in a seamless fashion without leaving behind any residual exogenous nucleotide sequence.

In one embodiment, one or more of the genes coding for the proteins known to function in fermentative pathways are inactivated through one or more mutations. Genes and enzymes that may be inactivated include: ldhA, lactate dehydrogenase; pflB, pyruvate-formate lyase; ackA, acetate kinase; adhE, alcohol dehydrogenase; furA, fumB, and fumC, fumarase isozymes and combinations thereof, such as ΔfumAB, ΔfumBC, ΔfumAC and ΔfumABC; ΔfrdABCD, fumarate reductase or various subunits, such as ΔfrdA, ΔfrdB, ΔfrdC, ΔfrdD or combinations thereof such as ΔfrdAB, ΔfrdBC, ΔfrdBD; mgsA, methylglyoxal synthase; poxB, pyruvate oxidase; sfcA, malic enzyme; pykA or pykF, pyruvate kinase; maeB, malic enzyme. It yet another aspect, genes which are functional homologues of the aforementioned genes may also be inactivated.

In one embodiment, biocatalysts are selected for their ability to produce malic acid at high titer, yield and volumetric productivity. One embodiment provides a biocatalyst capable of producing at least 1.0 mole of malic acid for every one mole of carbon source (e.g., glucose) consumed. Such biocatalysts may, optionally, have been selected using metabolic evolution.

The term "titer" means the molar concentration of a particular compound in the fermentation broth. Thus in the fermentation process for the production of malic acid, a titer of 100 mM would mean that the fermentation broth at the time of measurement contained 100 mMoles of malic acid per liter of the fermentation broth.

The term "yield" refers to the moles of particular compound produced per mole of the feedstock consumed during the fermentation process. Thus in the fermentative process for the production of malic acid using glucose as the feedstock, the term yield refers to the number of moles of malic acid produced per mole of glucose consumed.

The term "volumetric productivity" refers to the amount of particular compound in grams produced per unit volume per unit time. Thus a volumetric productivity value of 0.9 g $L^{-1}$ $h^{-1}$ for malic acid would mean that 0.9 gram of malic acid is accumulated in one liter of fermentation broth during an hour of growth.

The terms "titer," "yield," and "volumetric productivity" as used in this disclosure also include "normalized titer," "normalized yield," and "normalized volumetric productivity." In the determination of the normalized titer, normalized yield, and normalized volumetric productivity, the volume of the neutralizing reagents added to the fermentation vessel in order to maintain the pH of the growth medium is also taken into consideration.

The terms "genetically engineered" or "genetically modified" as used herein refers to the practice of altering the expression of one or more enzymes in a microorganism by manipulating its genomic DNA.

In one aspect, a process for the production of malic acid in commercially significant quantities from the carbon compounds by genetically modified bacterial strains (GMBS; also referred to as biocatalysts or genetically modified microorganisms) is provided. Microorganisms suitable for the production of malic acid can be cultured in one or two-step processes as disclosed herein.

The term "gene" includes the open reading frame of the gene as well as the upstream and downstream regulatory sequences. The upstream regulatory region is also referred as the promoter region of the gene. The downstream regulatory region is also referred as the terminator sequence region.

"Mutation" refers to genetic modifications done to the gene including the open reading frame, upstream regulatory region and downstream regulatory region. The gene mutations result in either an up regulation or a down regulation or complete inhibition of the transcription of the open reading frame (ORF) of the gene. Gene mutations can be achieved either by deleting the entire coding region of the gene (ORF) or a portion of the coding nucleotide sequence (ORF), by introducing a frame shift mutation within the coding region, by introducing a missense mutation, insertion of sequences that disrupt the activity of the protein encoded by the gene, by introducing a stop codon or any combination of the aforementioned gene mutations.

As used herein, the term "exogenous" is intended to mean that a molecule or an activity derived from outside of a cell is introduced into the host microbial organism. In the case of an exogenous nucleic acid molecule introduced into the microbial cell, the introduced nucleic acid may exist as an independent plasmid or may get integrated into the host chromosomal DNA. The exogenous nucleic acid coding for a protein may be introduced into the microbial cell in an expressible form with its own regulatory sequences such as promoter and terminator sequences. Alternatively, the exogenous nucleic acid molecule may get integrated into the host chromosomal DNA and may be under the control of the host regulatory sequences.

The term "endogenous" refers to the molecules and activity that are present within the host cell. When used in reference to a biosynthetic activity, the term "exogenous" refers to an activity that is introduced into the host reference organism. The source can be, for example, a homologous or heterologous encoding nucleic acid that expresses the referenced activity following introduction into the host microbial organism. If the nucleic acid coding for a protein is obtained from the same species of the microbial organism, it is referred to as homologous DNA. If the nucleic acid is derived from a different microbial species, it is referred as heterologous DNA. Irrespective of the nature of the DNA, whether it is homologous or heterologous, when introduced into a host cell, the DNA as well as the activity derived form that introduced DNA, is referred to as exogenous. Therefore, exogenous expression of an encoding nucleic acid can utilize either or both heterologous and homologous encoding nucleic acid.

The term "redox balance" refers to the ability of the cell to maintain the appropriate ratio of NADH to $NAD^+$. In other words, the cells are able to oxidize the NADH so that there is enough $NAD^+$ to oxidize the carbohydrate substrates during the anaerobic fermentative growth. During aerobic growth, the $NAD^+$ pool is regenerated through oxidative phosphorylation involving NADH. However, under anaerobic growth condition the regeneration of the $NAD^+$ pool is achieved only by means of manipulating the flow of carbon through various metabolic pathways inside the cell which could oxidize NADH.

One aspect provides GMBS showing impressive titers, high yield and significant volumetric productivity for malic acid when grown under fermentative conditions in minimal salt medium containing a carbon source as the substrate for fermentation process. The microorganisms disclosed herein can be employed in a single step production process using various sugars such as hexoses, pentoses, disaccharides and other carbon compounds such as glycerol. Alternatively, the GMBS can be employed in a two-step production process (e.g., an aerobic culture step followed by an anaerobic culture step) using various sugars such as hexoses, pentoses, disaccharides and other carbon compounds such as glycerol.

In one embodiment, the genetic modifications involve only the manipulation of genes within the native genome of the microorganisms. In that embodiment, no exogenous genetic material such as plasmid bearing antibiotic resistance genes or any other exogenous nucleotide sequences coding for certain enzyme proteins is introduced into the bacterial strains used as a biocatalysts for malic acid production.

Microorganisms suitable for genetic manipulation as disclosed herein include a number of bacterial families, including the Enterobacteriaceae family. Thus, suitable microorganisms are selected form the genera *Escherichia, Erwinia, Providencia*, and *Serratia*. Within the genus *Escherichia*, the species *Escherichia coli* can be used. Exemplary strains include *E. coli* B, *E. coli* C, *E. coli* W, or the like. *E. coli* strains capable of producing organic acids in significant quantities are well known in the art. For example, the U. S. Patent Application Publication No. 2009/0148914 provides strains of *E. coli* as a biocatalyst for the production of chemically pure acetate and/or pyruvate. The U.S. Patent Application Publication No. 2007/0037265 and U.S. Pat. No. 7,629,162 provide derivatives of *E. coli* KO11 strain constructed for the production of lactic acid. International Patent Application published under the Patent Cooperation Treaty No. WO 2008/115958 provides microorganism engineered to produce malate and succinate in minimal mineral salt medium containing glucose as a source of carbon in pH-controlled batch fermentation. In some other embodiments, bacteria that can be modified include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indices, Bacillus licheniformis, Bacillus subtilis, Bacillus amyloliquifaciens, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus retigeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus subtilis, Bacillus licheniformis, Bacillus amyloliqyefaciens, Bacillus coagulans, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri* and so forth. Various other embodiments allow for the use of non-ruminant bacterial cells. Such language allows for the use of any bacterial cell with the exception of those identified in Table 5. *E. coli* strains obtained from culture collections such as ATCC (American Type Culture Collection) can be genetically engineered and subsequently metabolically evolved to obtain a strain with an enhanced ability to produce malic acid in commercially significant amounts.

The microorganisms disclosed herein can be grown aerobically (in the presence of oxygen) or anaerobically (in the complete absence of oxygen) or microaerobically (with a minimal amount of oxygen supply). In the one embodiment, the microorganism selected for the production of malic acid is grown in an anaerobic condition. Alternatively, the microorganisms can be grown in a two-phase (dual-phase) growth regime, wherein the microorganism is initially grown in an aerobic growth condition to reach a certain level of cell growth before transferring it to the anaerobic growth condition to achieve the production malic acid in commercially significant quantities. During the dual-phase growth for the production of malic acid by GMBS, production and the accumulation of the malic acid occurs during the anaerobic fermentative growth phase.

The present invention combines the technique of specific genetic modifications with the process of metabolic evolution to obtain strains showing high yield, titer and volumetric productivity for malic acid production under, for example, anaerobic growth conditions in the mineral salt medium with a carbohydrate substrate. The genetically modified microbial strains obtained from genetic modifications may be subsequently grown in mineral salt medium with a carbohydrate source for several generations to select a clone with very high yield for malic acid production. This process for the growth-based selection of a clone with the most preferred phenotype is referred as metabolic evolution. During metabolic evolution, the genetically modified strain is repeatedly transferred into fresh minimal medium for a period of time to obtain a clone that exhibits fast cell growth, rapid consumption of different carbon sources, ability to use multiple sugars simultaneously, ability to tolerate toxic chemicals in the carbon source and high production yield and productivity of the desired organic acid coupled with the low production of other organic acids. During the metabolic evolution, attention is paid to select the clone with the desirable phenotypes discussed above. A clone resulting from the metabolic evolution showing a very good growth rate in mineral salts medium supplemented with a carbon source but that has not improved in the yield of the desired organic acid is not a desirable clone.

Genetic manipulations can be done in several different stages accompanied by metabolic evolution in between the stages of genetic manipulations. The genomic manipulations involve either altering the endogenous DNA sequences or completely removing specific DNA sequences from the genomic DNA. The genetic manipulations may also involve inserting a foreign DNA sequence within the genomic DNA sequence of the microorganism. Certain embodiments, the genetic manipulations are accomplished by means of removing specific DNA sequences from the genomic DNA of the microorganisms without introducing any foreign DNA. Certain genetic manipulations necessary to inactivate the expression of a gene coding for a particular protein product requires an insertion of a foreign DNA sequence into the genome of the microorganism to select a clone with the desired genetic modification. For example, exogenous antibiotic marker genes can be used to insertionally inactivate the endogenous genes and to select the clone with the desired genotype. In one embodiment of the present invention, the introduced exogenous DNA sequences are ultimately removed from the genomic DNA of the microorganism so that the microorganism at the end of the genetic engineering process would have no exogenous DNA in its resulting genomic DNA. Various genetic engineering techniques necessary for accomplishing the objectives of the preferred embodiment of the present invention have been described in detail in two different scientific publications (33, 34). The published U.S. Patent Applications with numbers US 2007/0037265 and US 2009/0148914 and the International patent application published under the Patent Cooperation Treaty with International Publication Number WO 2008/115958 also describe the genetic engineering techniques useful in practicing various embodiments of this present invention. These scientific publications as well as patent documents are herein incorporated by reference for the purpose of providing the details for genetic engineering techniques useful for the present invention.

In one embodiment of the present invention, one or more of the genes coding for the proteins known to function in fermentative pathways are inactivated through one or more genetic manipulations or genetic engineering techniques as discussed above. Genes and enzymes that may be inactivated include: ldhA, lactate dehydrogenase; pflB, pyruvate-formate lyase; ackA, acetate kinase; adhE, alcohol dehydrogenase; fumA, fumB, and fumC, fumarase isozymes and combinations thereof, such as fumAB, fumBC, fumAC and fumABC; frdABCD, fumarate reductase or various subunits, such as frdA, frdB, frdC, frdD or combinations thereof such as frdAB, frdBC, frdBD; mgsA, methylglyoxal synthase; poxB, pyruvate oxidase; sfcA, malic enzyme; pykA or pykF, pyruvate kinase; maeB, malic enzyme. It yet another aspect of the present invention, genes which are functional homologues of the aforementioned genes may also be inactivated. Additional genes and/or gene products, as set forth below, can also be inactivated in various aspects of the invention. During the aerobic growth, the microbial carbon metabolism involves glycolysis, tricarboxylic acid cycle and oxidative phosphorylation. The reduced enzyme co-factors such as NADPH and NADH are regenerated by the operation of oxidative phosphorylation accompanied by ATP production required for cell growth. Under anaerobic growth conditions for the production of malic acid, the regeneration of reduced cofactors NADPH and NADH is accomplished by directing the carbon flow into the tricarboxylic acid cycle and eliminating all of the fermentative pathways for regeneration of $NADP^+$ and $NAD^+$.

In one embodiment of the present invention, the carbon flow from PEP through fermentative pathways is prevented by mean of inactivating the genes coding for the enzymes involved in the fermentative pathway. The enzymes suitable for blocking the carbon flow through the fermentative pathway include ldhA, pflB, adhE, pflB, ackA, and poxB. The elimination of one or more of these genes is expected to reduce the carbon flow from PEP through the fermentative pathway. Inactivation of all these six genes is expected to block the carbon flow through the fermentative pathway. In another aspect of the present invention, the mgsA gene coding for the methylglyoxal synthase (MSG; responsible for the conversion of methylglyoxal to lactic acid) is also inactivated. GMBS may further comprise mutation of individual fumarate reductase subunits frdA, frdB, frdC, frdD, various combinations thereof (e.g., frdBC, frdAB, frdCD, frdABC, frdBCD, frdACD or frdABD) or mutation/deletion of frdABCD.

In yet another embodiment of the present invention, the functional homologues of the genes involved in the fermentative pathway are also inactivated besides inactivating the genes well known to be involved in one or other fermentative pathway. A propionate kinase with acetate kinase activity is encoded by the tdcD gene which is produced only for the degradation of threonine. However, during the anaerobic growth with 10% (w/v) glucose, the expression of tdcD could functionally replace ackA. In addition, the adjacent tdcE gene in the same operon is similar to pflB and encodes α-ketobutyrate formate lyase with pyruvate formate-lyase activity. In one aspect of the present invention, the tdcDE genes are inactivated to prevent the entry of carbon into fermentative pathway and to assure the flow of carbon into the TCA cycle.

In yet another embodiment of the present invention, besides preventing the operation of the fermentative pathways and increasing the flow of carbon within the TCA cycle towards malic acid production through genetic manipulations, the outward carbon flow from the TCA cycle to other metabolic pathways can also be blocked through genetic means to increase the malic acid production. For example, the flow of carbon from the TCA cycle into amino acid metabolism can be blocked in order to improve the carbon flow towards malic acid. The aspartate aminotransferase gene (aspC) transfers the amino group from glutamic acid to oxaloacetic acid in the synthesis of aspartic acid and thereby facilitates the outward flow of carbon from the TCA cycle. In one aspect of the present invention, the inactivation of the aspC and/or the aspA gene is followed to block the outward flow of carbon from the TCA cycle in order to improve the carbon flow from oxaloacetate towards malic acid production either through the oxidative or reductive arm of the TCA cycle.

The other outward flow of the carbon from TCA cycle occurs from malate. The decarboxylation of malate by malic enzyme (sfcA or maeB) results in the production of pyruvate. In one aspect of the present invention, the sfcA gene, maeB gene or both genes/gene products is/are inactivated to curtail the outward flow of carbon from TCA cycle. In yet another aspect of the present invention, one or more of the following gene or gene products are inactivated to prevent the outward flow of carbon from TCA cycle so as to enhance the accumulation of malic acid: aspC, maeB and sfcA.

Another aspect of the invention provides a method for manipulating the carboxylating enzymes present within the cell as a method to increase the malic acid yield during anaerobic fermentative growth. It is well known in the art that by means of introducing pyruvate carboxylase (pyc) from an exogenous source it is possible to carboxylate pyruvate to oxaloacetic acid. The microbial strains well suited for genetic manipulations such as E. coli do not have the pyc gene. The pyc genes derived from other bacterial species such as Rhizopium elti and Lactobacillus lacti can be introduced into the genetically modified E. coli strains to improve malic acid production.

Four different endogenous carboxylating enzymes are known in E. coli. Two of these enzymes are responsible for carboxylating phosphoenolpyruvate and two other enzymes are responsible for the carboxylation of pyruvate. The enzyme phosphoenolpyruvate carboxylase (ppc) carboxylates phosphoenolpyruvate to oxaloacetate which could enter into reductive arm of the TCA cycle to produce malate. The second carboxylating enzyme phosphoenolpyruvate carboxykinase (pck) also carboxylates phosphoenolpyruvate to produce oxaloacetate, but normally catalyzes the reverse reaction as it is not expressed in the presence of glucose. Any one of these two carboxylating enzymes present in the cell can be genetically manipulated to increase its enzymatic activity in order to improve the carbon flow from glycolytic cycle intermediates into the TCA cycle.

PEP carboxykinase (PCK) can be genetically manipulated to improve the flow of carbon into the TCA cycle. Previous studies have shown that increased expression of E. coli and Actinobacillus. succinogenes pck had no effect on succinate production (Kim et al., 2004; Millard et al., 1996). A recent study has demonstrated that increased expression of E. coli pck is detrimental for growth in minimal medium, decreasing the growth rate, the rate of glucose metabolism, and the yield of succinate. [Kwon et al., 2008). The advantage in improving the activity of pck lies in the fact that this enzyme while carboxylating phosphoenolpyruvate to oxaloacetate, results in the production of a molecule of ATP for every molecule of oxaloacetate produced. An increase in the ATP yield would increase the growth rate of the cells. GMBS (of any bacterial strain) in which pck expression has been genetically manipulated may further comprise mutation of individual fumarate reductase subunits frdA, frdB, frdC, frdD, various combinations thereof (e.g., frdBC, frdAB, frdCD, frdABC, frdBCD, frdACD or frdABD) or mutation/deletion of frdABCD. Additional genes encoding elements of the fermentative pathway may also be deleted.

The comparative analysis of phosphoenolpyruvate carboxykinase activity in a number of *E. coli* strains has revealed an increase in the PCK enzyme activity during metabolic evolution that resulted from an increase in the transcriptional activity of the pck gene. Such microorganisms are also useful for the production of malic acid by deletion or inactivation of fumarate reductase (FRD) activity. FRD activity can be inactivated by genetic manipulation of the frd genes (individual fumarate reductase subunits frdA, frdB, frdC, frdD, various combinations thereof (e.g., frdBC, frdAB, frdCD, frdABC, frdBCD, frdACD or frdABD) or mutation/deletion of frdABCD). Such strains would exhibit increased PCK activity, no fumarate reducatase activity and have the ability to produce malic acid as described in this application.

The recruitment of the native gluconeogenic pck for malate production can be achieved by any mutation that positively affects the transcription of the pck gene. An increase in the level of PCK activity can be achieved by means of expressing the pck gene in a multicopy plasmid with a native promoter or any other promoter sequence which is known to increase the gene's expression. Another way to increase the expression of the pck gene within the cell is to integrate additional copies of the pck gene using transposons. In another embodiment of the present invention, the native promoter of the pck gene can be replaced by some other promoter elements known to enhance the level of activity. An increased expression of pck gene can also be achieved either by mutation in the promoter region of the gene or by genetic manipulation of the regulatory elements that are known to interact with the promoter region of the pck gene. The gene coding for a regulator protein of the pck gene can be mutated or deleted or overexpressed in some way in order to increase the expression of pck gene. Previous results have indicated that a single point mutation (G to A transition at position-64 relative to the ATG start codon of pck gene in *E. coli*) could increase the transcription of the pck gene accompanied by a corresponding increase in the phosphoenolpyruvate carboxykinase enzyme activity. A similar increase in the pck gene expression can also achieved by genetically manipulating the genes coding for the proteins known to regulate the expression of pck gene. For example, Cra protein has been shown to activate the expression of the pck gene in *E. coli* (37). Similarly the csrA system (comprising csrA, csrB, csrC, csrD, uvrY or barA) has also been reported to regulate the level of pck and other genes involved in glucose metabolism by altering mRNA stability (32, 36, 38). These methods of introducing PCK activity can also be used for microorganisms (bacterial cells) that do not contain/have endogenous PCK activity.

Yet another genetic approach of the present invention to increase the growth-coupled malic acid production during the anaerobic fermentation process is concerned with the conservation of energy expended in sugar uptake by the biocatalysts. The microorganisms take up the sugars through a set of transporter proteins located on the cytoplasmic membrane (35). The microbial sugar transporters fall within three major categories. The largest group of sugar transporters in the bacteria is known as ATP binding cassette (ABC) transporters. As the name implies, the ABC transporters require a molecule of ATP for every molecule of sugar transported into the bacterial cell. XylFGH is an ABC transporter for the transport of xylose, a pentose sugar, into the cell. AraFGH is an ABC transporter for the transport of arabinose, yet another pentose sugar.

The second type of bacterial sugar transporters are grouped under Major Facilitator Super family (MFS). Within the MFS sugar transporters, two different categories of transporter are recognized. MFS includes $H^+$-linked symporters, $Na^+$-linked symporters-antiporters and uniporters. The trans-membrane protein Glf in *E. coli* is an example of uniporter. The GalP protein in *E. coli* is a $H^+$symporter for the transport of galactose, a hexose sugar, into the cell. GalP is a very well characterized symporter with 12 trans-membrane loops. GalP is also reported to have the ability to transport glucose across the cell membrane. AraE is a proton-linked symporter for the transport of arabinose across the cell membrane. Similarly XylE protein is a proton-linked symporter for the transport of xylose.

The third sugar transporter primarily responsible for the uptake of hexose sugars such as glucose is known as the phosphoenolpyruvate: carbohydrate phosphotransferase system (PTS). Transfer of the phosphoryl group from phosphoenolpyruvate (PEP) catalyzed by PTS drives the transport and phosphorylation of glucose and results in the formation of glucose 6-phosphate and pyruvic acid inside the cell. PTS generated pyruvic acid is apparently not recycled to PEP under aerobic culture conditions where glucose is the sole source of carbon. Rather, pyruvate is oxidized by way of the tricarboxylic acid cycle to carbon dioxide. Thus, for the transport of every single molecule of glucose, a molecule of PEP is consumed. In terms of cellular bioenergetics, the transport of sugars through PTS is an energy intensive process. Therefore in cells growing anaerobically, where there is a need to conserve the phosphoenolpyruvate content within the cells for the production of industrially useful chemicals, it is desirable to replace the PTS with some other sugar transporters not requiring a molecule of PEP for every molecule of sugar transported into the cell.

Besides these genes directly involved in the glycolysis, tricarboxylic acid cycle and glyoxylate shunt of microbial metabolic pathways, genetic manipulation of the genes involved in the uptake of carbon compounds useful as a source of energy for the synthesis of malic acid can also be used to?? either enhance the carbon uptake or to enhance the efficiency of energy utilization in organic acid production. For example the elimination of the glucose uptake by the phosphotransferase system (PTS) could help in reducing the energy spent on glucose uptake into the microbial cell. The energy conserved by manipulating the PTS can be channeled to improve the efficiency of organic acid production. The phosphotransferase system genes ptsH and ptsG can be manipulated to conserve the energy in glucose uptake and thereby improve the efficiency of malic acid production by microorganism.

PTS is comprised of two cytoplasmic components namely El and HPr and a membrane-bound component EII. *E. coli* contains at least 15 different EII complexes. Each EII component is specific to a sugar type to be transported and contains two hydrophobic integral membrane domains (C and D) and two hydrophilic domains (A and B). These four domains together are responsible for the transport and phosphorylation of the sugar molecules. EI protein transfers the phosphate group from PEP to HPr protein. EII protein transfers the phosphate group from phosphorylated HPr protein to the sugar molecule.

EI is encoded by the ptsI gene. HPr is encoded by the ptsH gene. The glucose-specific EII complex of enteric bacteria consists of two distinct proteins namely, $EIIA^{Glc}$ encoded by the gene err and the membrane-associated protein EIICB$^{Glc}$ encoded by the gene ptsG. The PTS mediated sugar transport can be inhibited by means of deleting or inactivating one or more of the genes coding for the proteins associated with PTS. With the inhibition the PTS-mediated glucose uptake, other systems for glucose uptake can be activated to assure the continued availability of glucose within the cell for the production of the industrially useful chemicals. For example, the glf gene coding for glucose permease, a glucose uniporter, has been shown to substitute for the loss of PTS mediated glucose uptake. Similarly the over expression of galP and glk genes are reported to enhance the glucose uptake and phosphorylation in a pts⁻ strain of E. coli. GalP is a symporter for the uptake of galactose, a hexose sugar. GalP has been reported to transport glucose in the pts⁻ strain. The significance of GalP mediated glucose uptake is evidence by the fact that the inactivation of galP gene in the pts⁻ mutant is found to be lethal (39). Glk is necessary to achieve the phosphorylation of the glucose molecule before it can enter into glycolysis. The expression of the GalP protein in the pts⁻ strain can be achieved either by expressing an exogenous gene under a constitutive promoter or by means of relieving the repression of the galP expression through mutations in genes coding for the repressor of the galP gene such as galS and gallR.

The invention also provides genetic approaches to enhance glycerol utilization in malic acid production. The glycerol uptake is mediated by the protein coded by the glpF gene. Once taken into the cell, glycerol can be phosphorylated by glycerol kinase encoded by the glpK gene and converted to dihydroxy acetone phosphate (DHAP) by the products of the glpD gene or the glpABC genes. Alternatively, glycerol can be oxidized by the protein coded by the gldA gene to produce dihydroxy acetone (DHA). The DHA is phosphorylated to DHAP by the proteins coded by dhaKLM operon. The phophoylation of DHA to DHAP by the proteins coded by dhaKLM is dependent on the availability of the phosphoenolpyruvate (PEP) pool. Since the phosphorylation of DHA requires PEP, it depletes the PEP available for PCK which directs the flow of carbon from PEP into the TCA cycle in order to assure proper redox balance. Preventing the flow of glycerol through the gldA and dhaKLM pathways in a bacterial cell having an increased PCK enzymatic activity could enhance malic acid yield using glycerol as the carbon source.

Accordingly, the following non-limiting embodiments are provided:

1. A bacterial cell comprising genetic modifications causing the inactivation of enzymatic activity for: lactate dehydrogenase; pyruvate-formate lyase; acetate kinase; alcohol dehydrogenase; and fumarate reductase.

2. The bacterial cell according to embodiment 1, further comprising genetic modifications causing the inactivation of enzymatic activity of methylglyoxal synthase and pyruvate oxidase.

3. The bacterial cell according to embodiment 1 or 2, further comprising genetic modifications causing the inactivation of enzymatic activity of a NAD-dependent and/or a NADP-dependent malic enzyme.

4. The bacterial cell according to embodiment 3, further comprising genetic modifications causing the inactivation of enzymatic activity of a fumarate hydratase.

5. The bacterial cell according to embodiment 4, further comprising genetic modifications causing the inactivation of enzymatic activity of a pyruvate kinase.

6. The bacterial cell according to embodiment 1, wherein said lactate dehydrogenase is encoded by ldhA; said pyruvate-formate lyase is encoded by pflB; said acetate kinase is encoded by ackA; said alcohol dehydrogenase is encoded by adhE; and said fumarate reductase is encoded by frdABCD.

7. The bacterial cell according to embodiment 1, wherein the enzymatic activity of fumarate reductase is inactivated by genetic modification of one or more fumarate reductase subunit.

8. The bacterial cell according to embodiment 7, wherein said genetic modification comprises a point mutation or a deletion in the coding sequence of said fumarate reductase subunit or insertion of an exogenous sequence into the coding region of said fumarate reductase subunit.

9. The bacterial cell according to embodiment 8, wherein said genetic modification comprises complete or partial deletion of frdA, frdB, frdC, frdD, frdAB, frdBC, frdABC, frdBCD or frdABCD.

10. The bacterial cell according to embodiment 2, wherein said methylglyoxal synthase is encoded by mgsA and pyruvate oxidase is encoded by poxB and the enzymatic activity of methylglyoxal synthase and pyruvate oxidase is inactivated by a genetic modification comprising a point mutation or a deletion in the coding sequence of one or both of said enzyme(s) or insertion of an exogenous sequence into the coding region of one or both of said enzyme(s).

11. The bacterial cell according to embodiment 10, wherein said genetic modification comprises complete or partial deletion of mgsA and poxB.

12. The bacterial cell according to embodiment 3, wherein said NADP-dependent malic enzyme is encoded by maeB and said NAD-dependent malic enzyme is encoded by sfcA and the enzymatic activity of said malic enzyme is inactivated by a genetic modification comprising a point mutation or a deletion in the coding sequence of one or both of said malic enzyme(s) or insertion of an exogenous sequence into the coding region of one or both of said malic enzyme(s).

13. The bacterial cell according to embodiment 10, wherein said genetic modification comprises complete or partial deletion of maeB, sfcA or both maeB and sfcA 14. The bacterial cell according to embodiment 4, wherein said fumarate hydratase is encoded by fumA, fumB or fumC and the enzymatic activity of said fumarate hydratase is inactivated by a genetic modification comprising a point mutation or a deletion in the coding sequence of one or more of said fumarate hydratases or insertion of an exogenous sequence into the coding region of one or more of said fumarate hydratases.

15. The bacterial cell according to embodiment 14, wherein said genetic modification comprises complete or partial deletion of one or more of fumA, fumB or fumC.

16. The bacterial cell according to embodiment 15, wherein said genetic modification comprises complete or partial deletion in the following combinations of fumarate hydratases: fumAB, fumBC, fumAC or fumABC.

17. The bacterial cell according to embodiment 5, wherein said pyruvate kinase is encoded by pykA or pykF and the enzymatic activity of said pyruvate kinase is inactivated by a genetic modification comprising a point mutation or a deletion in the coding sequence of one or more of said pyruvate kinase(s) or insertion of an exogenous sequence into the coding region of one or more of said said pyruvate kinase(s).

18. The bacterial cell according to embodiment 17, wherein said genetic modification comprises complete or partial deletion in pykA, pykF or both pykA and pykF.

19. The bacterial cell according to any one of embodiments 1, 2 or 4-18, wherein said bacterial cell comprises increased levels of phosphoenol pyruvate carboxykinase (pck) gene transcripts, said transcripts encoding active phosphoenol pyruvate carboxykinase (PCK) and wherein said cell exhibits increased PCK activity.

20. The bacterial cell according to embodiment 3, wherein said bacterial cell comprises increased levels of phosphoenol pyruvate carboxykinase (pck) gene transcripts, said transcripts encoding active phosphoenol pyruvate carboxykinase (PCK) and wherein said cell exhibits increased PCK activity.

21. The bacterial cell according to any one of embodiments 1-20, wherein said bacterial cell is a non-ruminant bacterial cell.

22. The bacterial strain according to any one of embodiments 1-21, wherein said bacterium is *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Bacillus licheniformis, Bacillus subtilis, Bacillus amyloliquifaciens, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus licheniformis, Bacillus subtilis, Bacillus amyloliquifaciens, Bacillus coagulans, Escherichia freundii, Microbacterium ammoniaphilum, Serratia marcescens, Salmonella typhimurium, Salmonella schottmulleri,* or *Xanthomonas citri.*

23. The bacterial cell according to embodiment 19 or 20, wherein increased levels of said pck transcripts result from replacement of native regulatory sequences with altered regulatory sequences of the pck gene that increase pck transcription.

24. The bacterial cell according to embodiment 23, wherein said regulatory sequences are in the promoter region of said pck gene.

25. The bacterial cell according to embodiment 24, wherein said increased levels of said pck transcripts result from one or more mutations in the promoter region of the pck gene.

26. The bacterial cell according to embodiment 25, wherein said one or more mutations are point mutations comprising replacement of nucleotide A with nucleotide G at position 68 up stream of the pck gene start codon.

27. The bacterial cell according to embodiment 23 or 24, wherein increased levels of said pck transcripts result from replacement of the native promoter sequence with an exogenous promoter sequence.

28. The bacterial cell according to embodiment 27, wherein said exogenous promoter is a constitutive promoter.

29. The bacterial cell according to embodiment 27, wherein said exogenous promoter is an inducible promoter.

30. The bacterial cell according to embodiment 29, wherein the said inducible promoter is a lac promoter.

31. The bacterial cell according to any one of embodiments 1-30, further comprising one or more genetic modification that disrupts the functioning of PEP-dependent phosphotransferase system.

32. The bacterial cell according to embodiment 31, wherein said genetic modification is in one or more genes coding for the structural components of PEP-dependent phosphotransferase system.

33. The bacterial cell according to embodiment 31, wherein said genetic modification is in one or more genes coding for proteins that regulate the expression of PEP-dependent phosphotransferase system.

34. The bacterial cell according to embodiment 31, wherein the said genetic modification is in one or more genes selected from the group consisting of ptsG, ptsH, ptsI, crr and crp.

35. The bacterial cell according to any one of embodiments 1-30, further comprising: (a) one or more genetic modification that disrupts the functioning of PEP-dependent phosphotransferase system; and (b) one or more genetic modifications that upregulate the expression of one or more genes encoding sugar transporters.

36. The bacterial cell according to embodiment 35, wherein said sugar transporter is a member of ATP binding cassette transporters.

37. The bacterial cell according to embodiment 35, wherein said sugar transporter is a member of major facilitator super family.

38. A genetically modified bacterial cell, wherein said genetically modified bacterial cell is XZ316, XZ372, XZ347, XZ654, XZ658, XW00 or XW03.

39. An *Escherichia coli* bacterial strain comprising: (a) ΔldhA; (b) ΔackA; (c) ΔadhE; (d) ΔpflB; (e) ΔfrdBC; (f) ΔpoxB; (g) ΔmgsA (h) ΔsfcA; (i) ΔmaeB; (j) ΔfumB; and (k) ΔfumAC.

40. The *Escherichia coli* bacterial strain according to embodiment 39, further comprising ΔpykA, ΔpykF or both ΔpykA, ΔpykF.

41. An isolated bacterial cell, said bacterial cell lacking fumarate reductase (FRD) activity and having increased levels of phosphoenol pyruvate carboxykinase (pck) gene transcripts, said transcripts encoding active phosphoenol pyruvate carboxykinase (PCK) and wherein said cell exhibits increased PCK activity.

42. The bacterial cell according to embodiment 41, wherein said bacterial cell is a non-ruminant bacterial cell.

43. The bacterial cell according to embodiment 41, wherein said bacterium is *Escherichia coli, Gluconobacter oxydans, Gluconobacter asaii, Achromobacter delmarvae,*

*Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Bacillus licheniformis, Bacillus subtilis, Bacillus amyloliquifaciens, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus licheniformis, Bacillus subtilis, Bacillus amyloliquifaciens, Bacillus coagulans, Escherichia freundii, Microbacterium ammoniaphilum, Serratia marcescens, Salmonella typhimurium, Salmonella schottmulleri, or Xanthomonas citri.*

44. The bacterial cell according to embodiment 41, wherein increased levels of said pck transcripts result from replacement of native regulatory sequences with altered regulatory sequences of the pck gene that increase pck transcription.

45. The bacterial cell according to embodiment 44, wherein said regulatory sequences are in the promoter region of said pck gene.

46. The bacterial cell according to embodiment 41, wherein said increased levels of said pck transcripts result from one or more mutations in the promoter region of the pck gene.

47. The bacterial cell according to embodiment 46, wherein said one or more mutations are point mutations comprising replacement of nucleotide A with nucleotide G at position 68 up stream of the pck gene start codon.

48. The bacterial cell according to embodiment 41, wherein increased levels of said pck transcripts result from replacement of the native promoter sequence with an exogenous promoter sequence.

49. The bacterial cell according to embodiment 48, wherein said exogenous promoter is a constitutive promoter.

50. The bacterial cell according to embodiment 48, wherein said exogenous promoter is an inducible promoter.

51. The bacterial cell according to embodiment 48, wherein the said inducible promoter is a lac promoter.

52. The bacterial cell according to embodiment 41, further comprising one or more genetic modification that disrupts the functioning of PEP-dependent phosphotransferase system.

53. The bacterial cell according to embodiment 52, wherein said genetic modification is in one or more genes coding for the structural components of PEP-dependent phosphotransferase system.

54. The bacterial cell according to embodiment 52, wherein said genetic modification is in one or more genes coding for proteins that regulate the expression of PEP-dependent phosphotransferase system.

55. The bacterial cell according to embodiment 52, wherein the said genetic modification is in one or more genes selected from the group consisting of ptsG, ptsH, ptsI, crr and crp.

56. The bacterial cell according to embodiment 41, further comprising: (a) one or more genetic modification that disrupts the functioning of PEP-dependent phosphotransferase system; and (b) one or more genetic modifications that upregulate the expression of one or more genes encoding sugar transporters.

57. The bacterial cell according to embodiment 57, wherein said sugar transporter is a member of ATP binding cassette transporters.

58. The bacterial cell according to embodiment 56, wherein said sugar transporter is a member of major facilitator super family.

59. The bacterial cell according to embodiment 41, further comprising genetic modification leading to the inactivation of gene expression in one or more genes involved in the fermentative pathway.

60. The bacterial cell according to embodiment 41, further comprising genetic modification leading to the inactivation of gene expression in:

a) one or more genes selected from the group consisting of adhE, ldhA, pflB, mgsA, ackA, sfcA, maeB, fumA, fumB, fumC and poxB; or b) adhE, ldhA, pflB, mgsA, ackA, sfcA, maeB, fumA, fumB, fumC, poxB and one or more of the following genes or combinations of genes: frdA, frdB, fdrC, frdD, frdAB, frdAC, frdAD, frdBC, frdBD, frdCD, frdABC, frdCBD, frdACD, frdABCD.

61. The bacterial cell according to embodiment 41, further comprising: (a) one or more genetic modification that disrupts the functioning of PEP-dependent phosphotransferase system; and (b) mutation in one or more genes involved in the fermentative pathway.

62. The bacterial cell according to embodiment 41, further comprising: (a) genetic modification in one or more genes selected from a group consisting of ptsG, ptsH, ptsI, crr and crp; and (b) genetic modifications leading to the inactivation of gene expression in:

i) one or more genes selected from a group consisting of adhE, ldhA, pflB, mgsA, ackA, sfcA, maeB, fumA, fumB, fumC, frdA, frdB, fdrC, frdD, frdAB, frdAC, frdAD, frdBC, frdBD, frdCD, frdABC, frdCBD, frdACD, frdABCD and poxB; or ii) adhE, ldhA, pflB, mgsA, ackA, sfcA, maeB, fumA, fumB, fumC, poxB and one or more of the following genes or combinations of genes: frdA, frdB, fdrC, frdD, frdAB, frdAC, frdAD, frdBC, frdBD, frdCD, frdABC, frdCBD, frdACD, frdABCD.

63. The bacterial cell according to embodiment 41, further comprising genetic modification in one or more genes associated with the operation of the TCA cycle.

64. The bacterial cell according to embodiment 41, further comprising genetic modification in one or more genes selected from the group consisting of aspA and aspC.

65. The bacterial cell according to any preceding embodiment, further comprising:
   a) a mutation in gldA gene;
   b) a mutation in dhaKLM operon;
   c) (i) a mutation in gldA; and (ii) a mutation in dhaKLM operon;
   d) (i) a mutation in gldA; (ii) a mutation in dhaKLM operon; and (iii) a mutation in one or more genes coding for a protein in phosphotransferase system; or
   e) (i) a mutation in gldA; (ii) a mutation in dhaKLM operon; (iii) a mutation in one or more genes coding for a protein in phosphotransferase system; and (iv) a mutation in one or more genes coding for the proteins involved in fermentative pathway.

66. A method of producing malic acid comprising:
   a) culturing a bacterial strain according to any one of embodiments 1-65 in a carbon source;
   b) allowing said bacteria to metabolize said carbon source; and
   c) isolating malic acid.

67. The method according to embodiment 66, wherein said bacterial strain is cultured in anaerobic condition, aerobic condition, microaerobic condition or combinations thereof.

68. The method according to embodiment 67, wherein said bacterial strain is cultured aerobically followed by anaerobic culture.

69. The method according to embodiment 66, 67 or 68, wherein said bacterial strain is cultured in minimal salt growth medium.

70. The method according to embodiment 69, wherein said minimal salt growth medium comprises between 2% and 20% (w/v) carbon source.

71. The method according to embodiment 67, wherein the said carbon source is glucose, fructose, xylose, arbinose, galactose, mannose, rhamnose, sucrose, cellobiose, hemicelluloses, glycerol or combination thereof.

72. A bacterial cell or method according to any one of embodiments 1-37 or 41-71, wherein said bacterial strain is *Bacillus licheniformis, Bacillus subtilis, Bacillus amyloliquifaciens, E. coli B, E. coli C, E. coli W*, or the like.

Microorganisms were deposited with the Agricultural Research Service Culture Collection, 1815 N. University Street, Peoria, Ill., 61604 U.S.A (Table 6). These cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The following examples are provided as way of illustrating the present invention. These inventions in no way limit the scope of this invention. A person experienced in the field of industrial microbiology would be able to practice the present invention in several different embodiments without violating the spirit of the present invention.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

L-Malate Production by Metabolically Engineered *Escherichia Coli*

Materials and Methods

Strains, Media and Growth Conditions

Strains used in this study are listed in Table 2. KJ060 and KJ073 were previously engineered for succinate production (12). During strain construction, cultures were grown aerobically at 30° C., 37° C., or 39° C. in Luria broth (per liter: 10 g Difco tryptone, 5 g Difco yeast extract, and 5 g NaCl) containing 2% (w/v) glucose or 5% (w/v) arabinose. Ampicillin (50 mg liter$^{-1}$), kanamycin (50 mg liter$^{-1}$), or chloramphenicol (40 mg liter$^{-1}$) were added as needed.

Genetic Methods

Chromosomal genes were deleted seamlessly without leaving segments of foreign DNA as described previously (13, 30). Red recombinase technology (Gene Bridges GmbH, Dresden, Germany) was used to facilitate chromosomal integration. Plasmids and primers used during construction are listed in Table 2.

Enzyme Assays

Cells were grown in pH-controlled fermenters and harvested by centrifugation (70% of the maximal cell density; 7,000 g for 5 min, 4° C.) for the determination of fumarase activity. Cells were washed twice in 50 mM sodium phosphate buffer (pH 7.0) and disrupted using a Fastprep-24 (MP Biomedicals, Solon, Ohio) in the presence of 1 mM dithiothreitol (DTT). After clarification at 13,000 g (10 min, 4° C.), protein concentration was determined by the BCA method (Pierce Chemical, Rockville, Ill.) using bovine serum albumin as a standard. Fumarase activity was determined by measuring the conversion of malate to fumarate (extinction coefficient of 2,530 M$^{-1}$ cm$^{-1}$) (26). The reaction mixture contained 100 mM sodium phosphate buffer (pH 7.0), 50 mM malate and 1 mM DTT. One unit of activity is the amount of protein required to produce 1 µmol of fumarate per min. Note that DTT was essential to preserve activity with the Fastprep-24 bead disruptor.

L-specific and D-specific lactate dehydrogenases enzymes (Sigma Scientific, St. Louis, Mo.) were used to determine the chirality of lactate produced during fermentation. Reaction mixtures contained 200 mM Tricine buffer (pH 9.0), 5.5 mM NAD$^+$, and 1 U of commercial enzyme. Activity was measured by monitoring the formation of NADH at 340 nm (10). Lactate dehydrogenase activity from different strains was determined by measuring the conversion of pyruvate to lactate by oxidizing NADH (extinction coefficient of 6,220 M$^{-1}$ cm$^{-1}$) (10). Reaction mixtures contained 200 mM phosphate buffer (pH 7.0), 0.2 mM NADH and 1 mM Pyruvate (10).

Fermentation

Strains were grown without antibiotics at 37° C. in NBS (New Brunswick Scientific) mineral salts medium (3) supplemented with 2% or 5% (w/v) glucose and 100 mM potassium bicarbonate unless stated otherwise. Acetate (10 mM) was also included to improve growth. Pre-inocula for fermentations were grown by transferring fresh colonies into a 250 ml flask (100 ml NBS medium, 2% glucose). After 16 h (37° C., 120 rpm), this culture was diluted into a small 500 ml fermentation vessel containing 300 ml NBS medium (5% glucose, 100 mM potassium bicarbonate) to provide an inoculum of 0.033 g cell dry wt (CDW) liter$^{-1}$. For microaerobic process, fermentation was carried out in a 3-liter bioreactor (BioFlo 110, New Brunswick Scientific, Edison, N.J.) containing 1.5-liter NBS medium (5% glucose, 100 mM potassium bicarbonate). The inoculum was 0.017 g cell dry wt (CDW) liter$^{-1}$ with low aeration (0.1 vvm) to provide microaerobic conditions.

A two-stage process was also investigated using a 3-liter bioreactor (BioFlo 110) containing 1.2-liter NBS medium (5% glucose, 100 mM potassium bicarbonate; inoculum of 0.017 g cell dry wt CDW liter$^{-1}$). An air flow of 1.0 vvm was used for the initial aerobic growth. After 16 h (cell mass of 2.5 g liter$^{-1}$), air flow was stopped and incubation continued for anaerobic malate production. All fermentations were maintained at pH 7.0 by the automatic addition of base containing additional $CO_2$ (base for neutralization: 2.4 M potassium carbonate and 1.2 M potassium hydroxide).

Analysis

Cell dry weight was estimated by measuring optical density at 550 nm (OD550). Organic acids and glucose were measured by HPLC (30).

Results:

Inactivating Fumarase for Malate Production

E. coli KJ060 and derivatives were previously engineered in our lab for the production of succinate (12). In these engineered strains, the phosphotransferase system is inactive and phosphoenolpyruvate (PEP) is carboxylated to oxaloacetate (OAA) by PEP carboxykinase (pck), conserving energy as ATP. OAA is reduced by malate dehydrogenase (mdh), and so forth (FIG. 1). Based on this central pathway, elimination of fumarase activity would be expected to cause the accumulation of malate.

E. coli contains three fumarase isoenzymes encoded by fumB and fumAC (15, 26). Fumarase C is the dominant enzyme during aerobic growth and oxidative metabolism, but has low activity during anaerobic growth. Fumarase A is the dominant isoenzyme under microaerobic conditions (1 to 2% oxygen) and is also synthesized under anaerobic condition (25). Fumarase B is induced under anaerobic conditions where it serves as the dominant isoenzyme during fermentation. Based on inspection of this pathway (FIG. 1A) and published literature (rational design), inactivation of the fumB encoded isoenzyme would be expected to block the fermentative production of fumarate and accumulate malate as the primary reduced product. However, this did not occur after deletion of fumB in KJ060 (strain XZ273) and succinate remained as the dominant product (Table 3). Succinate yield and cell yield were both reduced in XZ273 by over 60%, consistent with FumB serving as the dominant isoenzyme during fermentation (13, 26). Deletion of genes encoding all three isoenzymes (strain XZ276) reduced succinate production by 97% and cell yield by 75% as compared to KJ060, with the accumulation of a small amount of malate (27 mM) after 6 days. With further incubation, this malate was converted to succinate despite the inactivation of the three known fumarase genes.

Strain XZ276 was subcultured at 24-h intervals for two weeks during which time growth improved substantially. A clone was isolated and designated XZ277. Strain XZ277 lacking all three fumarase isoenzymes produced 71 mM succinate after 2 days and no detectable malate (Table 3).

Succinate Accumulation in Strain XZ277 (ΔfumAC, ΔfumB)

Figure 2:
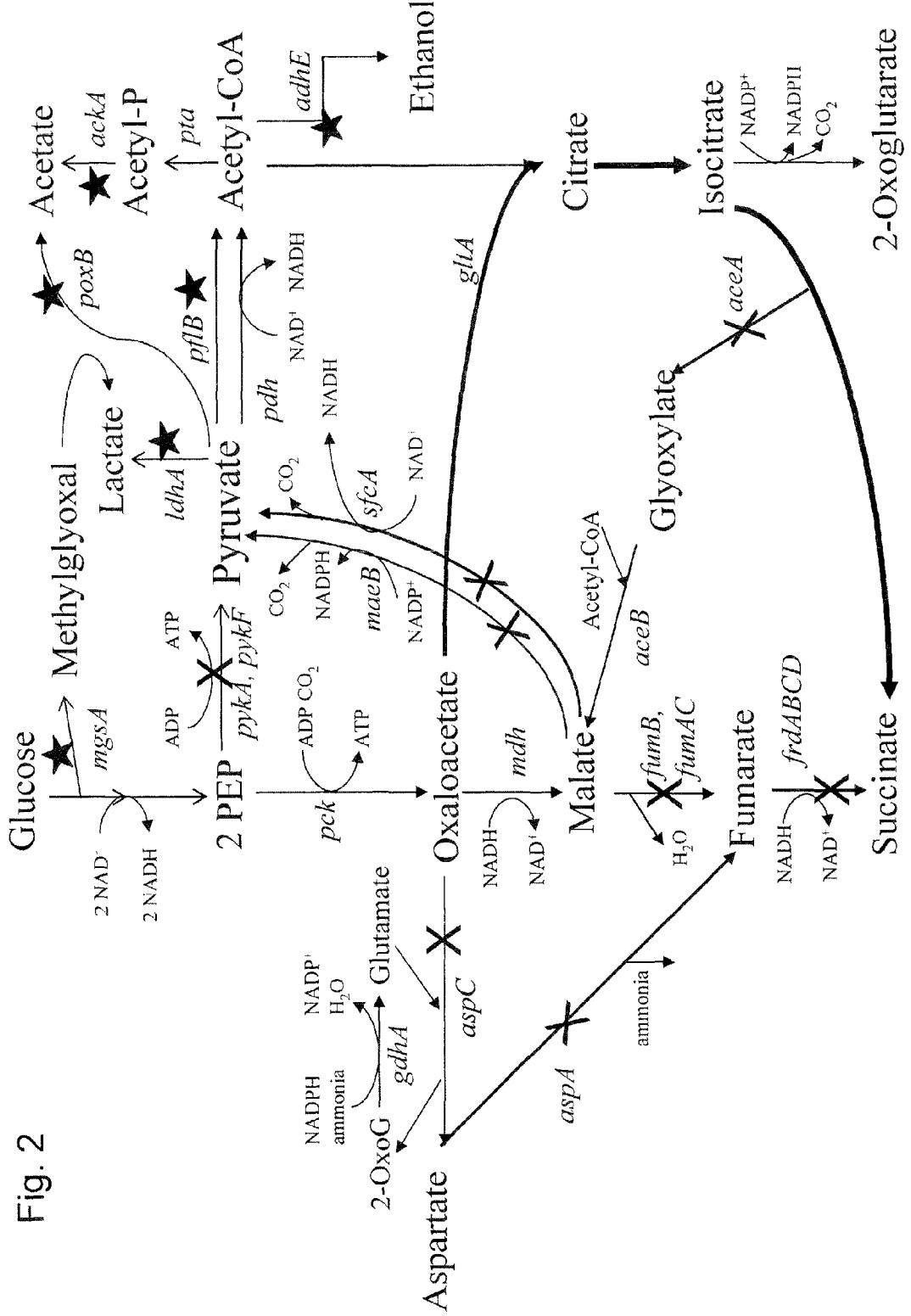
FIG. 2. Pathways concerned with malate metabolism and succinate production. The native fermentation pathway produces malate as an intermediate between oxaloacetate and fumarate. Fumarate is subsequently reduced to succinate. Gray arrows represent alternative routes to succinate which do not involve malate. Succinate can be produced from oxaloacetate through either an aspartate bypass (aspartate aminotransferase and aspartase) or by using the glyoxylate bypass (citrate synthase, aconitate hydratase and isocitrate lyase). Some intermediate steps in glycolysis have been omitted for clarity. Original gene deletions in the succinate-producing parent (KJ073) are marked with a star. Sites of new deletions in this paper are marked by an X. Abbreviations: PEP, phosphoenolpyruvate; 2-OxoG, 2-oxoglutarate; acetyl-CoA, acetyl-Coenzyme A.

Five mechanisms can be readily envisioned that could be responsible for succinate accumulation in fumarase deleted strains (FIG. 2). Aspartate metabolism could be activated. A combination of aspartate transaminase (aspC) and aspartate ammonia-lyase (aspA) could serve as a bypass route to malate (and succinate) without producing fumarate. The glyoxylate bypass could be activated by the deletion of fumarase genes and convert oxaloacetate and acetyl~CoA into malate and succinate by using citrate synthase (gltA), aconitate hydratase (acnA and acnB), isocitrate lyase (aceA), and malate synthase (aceB). E. coli could have a cryptic gene encoding fumarase activity. E. coli could use a more complex (unexplored) pathway to succinate. Alternatively, small amounts of malate could be spontaneously dehydrated to fumarate (ΔG=+1.3 kcal mol$^{-1}$) (9) and reduced to succinate to provide an energetically favorable process.

Potential conversion of malate to fumarate by aspartic acid metabolism (aspartate bypass) or by the glyoxylate bypass was investigated by deleting key genes. Strains XZ278, XZ280 and XZ282 were constructed by deleting aspA, aspC and aced in XZ277, respectively. After 2 days of fermentation, all strains produced primarily succinate and very little malate (Table 3), eliminating the activation of either pathway as a source of succinate.

Fumarase activities were measured in cell lysates of strain KJ060, XZ273 (KJ060 with fumB deletion), and XZ277 (KJ060 containing deletions in fumAC and fumB). Under substrate-saturating conditions, the fumarase activity in XZ273 (0.13±0.03 U mg$^{-1}$) was about 20% of fumarase activity in KJ060 (0.60±0.03 units mg$^{-1}$). Little activity was detected in XZ277 (0.00015 U mg$^{-1}$±0.00002) in which all three fumarase genes were deleted. Similar low levels were also observed for boiled lysates of KJ273 (<0.0001 units mg$^{-1}$) and bovine serum albumin, consistent with the absence of activity from a cryptic fumarase gene.

Although the net rate of spontaneous dehydration was essentially below detection, it remains possible that succinate is produced in the malate dehydrogenase negative strain by coupling the energetically favorable reduction of fumarate. With this route, inactivation of fumarate reductase should result in the accumulation of malate in the presence or absence of fumarase activity.

Deletion of Fumarate Reductase Promoted Malate and Pyruvate Accumulation

An improved succinate strain (KJ073) became available during the course of this study (11). This strain is a derivative of KJ060 that contains additional mutations in methylglyoxal synthase (ΔmgsA) and pyruvate oxidase (Δpox). Deletion of fumarate reductase in KJ060 and KJ073 (XZ372 and XZ316, respectively) did not cause accumulation of the substrate, fumarate, in either strain. However, this mutation eliminated over 90% of succinate production and promoted the accumulation of malate (Table 4), an earlier intermediate in the pathway. Smaller amounts of succinate and two redox-neutral products (acetate and pyruvate) were also produced. These results establish fumarate as an intermediate in succinate production despite the absence of a fumarase activity.

Sugar metabolism, cell yield, and succinate production were higher in KJ073 than in KJ060 (Table 4) and this strain was used in further studies to engineer improvements in malate production.

Pyruvate Accumulation in XZ316 Attributed to Malic Enzymes (scfA, maeB)

Conversion of malate to pyruvate is a thermodynamically favorable reaction (9). Although genes encoding malic enzymes (gluconeogenic) have been shown to be repressed by glucose during oxidative metabolism (14, 24), these enzymes represent potential routes to pyruvate (FIG. 2). There are two malic enzymes in *E. coli*, $NAD^+$-dependent SfcA and $NADP^+$-dependent MaeB. Both genes were sequentially deleted. Deletion of sfcA to produce strain XZ347 increased cell yield by 20% and increased malate production to 70 mM, 3-fold that of the parent XZ316. Subsequent deletion of the NADPH-linked malic enzyme (maeB) to produce XZ654 further increased malate yield but decreased malate titer, glucose metabolism, and cell yield. With the deletion of both genes (XZ654), pyruvate production was substantially eliminated (3 mM) establishing SfcA and MaeB as the primary sources of pyruvate. Thus both malic enzymes participate in glucose fermentation in addition to their role in gluconeogenesis during oxidative metabolism.

Deletion of Fumarase Isoenzymes in a Fumarate Reductase Mutant

Malate accumulated as a primary fermentation product after deletion of fumarate reductase (Table 3 and Table 4). Since fumarase activity is not required for malate production, further deletion of ΔfumAC and ΔfumB fumarase genes would seem redundant with no expected consequence. However, deletion of the three fumarase genes in strain XZ654 to produce XZ658 doubled cell yield (127% increase) and increased the malate titer by 4-fold (Table 4). This was accompanied by production of high lactate levels.

Lactate Accumulation Reduced by Pyruvate Kinase Deletions

Deletion of genes encoding the three fumarase isoenzymes (XZ658) caused a large and unexpected increase in lactate (78 mM; Table 4) despite the absence of lactate dehydrogenase (ΔldhA) and methylglyoxal synthase (ΔmgsA). Testing with chiral-specific lactate dehydrogenases indicated that only the D-lactate enantiomer was present. No lactate dehydrogenase activity could be detected in disrupted cells of XZ658 and the pathway leading to this D-lactate remains unknown. However, we observed that the addition of pyruvate (57 mM) to the fermentation medium increased the accumulation of D-lactate (and malate), cell yield, and the lactate/malate ratio. The effects of added pyruvate are complex and may be quite indirect due to its central role in metabolism.

Deletion of pykA and pykF were tested as a means of reducing the supply of pyruvate from PEP (Table 4). Deletion of either isoenzyme of pyruvate kinase reduced lactate production by over 90%. Cell yield and succinate production were also decreased by deletion of either pykA or pykF. Together, these results indicate both isoenzymes of pyruvate kinase function during glucose fermentation and that lactate production is related in part to an excess supply of pyruvate.

Improving the Production of Malate

Although malate was the dominant fermentation product of XZ658 (FIG. 1B), cell growth (0.75 g/L) and malate productivity (0.15 g $liter^{-1}$ $h^{-1}$) were low in comparison to our previous biocatalysts for succinate (12-13, 31) and lactate (8) production (Table 4). Microaerobic (3-4) and two-stage processes (aerobic cell growth followed by anaerobic fermentation) were investigated as approaches to improve malate production. After 6 days under microaerobic conditions (0.1 vvm air), malate production (120 mM) and malate yield (0.49 mol per mol glucose) were even poorer than observed during anaerobic fermentations (Table 4). A two stage process proved more effective for malate production. Cells were grown aerobically (1.0 vvm air) for 16 h (2.5 g $liter^{-1}$ dcw) and then shifted to anaerobic conditions for malate production (72 h). With this approach, 253 mM malate was produced with a yield of 1.42 mol per mol glucose. Productivity during the anaerobic phase averaged 0.47 g $liter^{-1}$ $h^{-1}$.

Discussion:

None of the natural malate-producing microorganisms appears suitable for large-scale commercial production due to either toxin production (aflatoxin; *A. flavus*) or dependence on complex medium and low yields (*Z. rouxii*) (1, 25) (Table 1). *S. cerevisiae* and *E. coli* are excellent platforms for bio-based chemicals and both have been investigated as biocatalysts for malate production (17, 28). *S. cerevisiae* was engineered for aerobic malate production by overexpressing pyruvate carboxylase, cytosolic malate dehydrogenase, and a malate transporter from *Schizosaccharomyces pombe*. This strain produced 59 g $liter^{-1}$ malate in flask cultures after 192 hours (28). However, the malate yield (0.42 mol $mol^{-1}$) and productivity (0.29 g $liter^{-1}$ $h^{-1}$) were low. *E. coli* was previously engineered for aerobic malate production by overexpressing *Mannheimia succiniciproducens* phosphoenolpyruvate carboxykinase and inactivating acetate production (17). Although the productivity was high (0.74 g $liter^{-1}$ $h^{-1}$), the final titer and yield were low (9.25 g $liter^{-1}$ and 0.56 mol respectively).

Several metabolically engineered *E. coli* strains were previously constructed for the efficient production of succinate from glucose under anaerobic conditions (12-13). Two key genetic changes were subsequently identified (29, 31). The native gluconeogenic phosphoenolpyruvate carboxykinase was recruited as the primary carboxylation reaction by mutational activation, conserving energy as additional ATP. The native glucose phosphoenolpyruvate-dependent phosphotransferase system was inactivated and replaced with the native GalP permease and glucokinase, increasing the availability of PEP for carboxylation to OAA. These changes are also important for efficient malate production, an intermediate in the fermentative succinate pathway. By adding deletions to inactivate fumarate reductase, malic enzymes, and fumarase isoenzyme, the fermentation of glucose has been substantially redirected to produce malate (Table 4). The best resulting strain, XZ658 (FIG. 1B), produced malate as the major fermentation product with a yield of 1.0 mol per mol glucose under anaerobic condition. This yield was increased to 1.42 mol $mol^{-1}$ using a two-stage process (aerobic growth followed by anaerobic fermentation), a higher yield than previously reported (Table 1). Malate productivity with XZ658 was 0.47 g $liter^{-1}$ $h^{-1}$, too low for most commercial uses but comparable to the best natural malate-producing microorganisms (Table 1). The titer of malate with the parent succinate-producing strain (KJ073) was less than 0.5 mM. Through metabolic engineering and the use of a two-stage process, this was increased by over 500-fold (XZ658).

Initial rational designs were surprisingly ineffective for the design of a malate biocatalyst. Gene deletions often produced unexpected results. Deletion of the three fumarase genes did not cause the accumulation of malate but, instead, caused the accumulation of succinate as the primary product. Similarly, deletion of the furmarate reductase genes did not cause the accumulation of the fumarate but instead resulted in the accumulation of malate. The primary basis for both results appears to center on the reversibility of the hydration reaction for interconversion of malate and fumarate even in the absence of fumarase. Although the thermodynamic equilibrium favors hydration ($\Delta G=-1.3$ kcal mol$^{-1}$) (9), this reaction is reversible under physiological conditions and appears to proceed at low rates even in the absence of a fumarase enzyme. During fermentative succinate production, this reaction is pulled in the direction of fumarate by abundant reductant and coupling with fumarate reductase, even without a functional fumarase. Malate accumulated only in mutants lacking fumarate reductase, with or without a functional fumarase. It is interesting to note that strains were readily developed which accumulated malate or succinate in fermentation broth at relatively high concentrations. Both of these dicarboxylic acids can be actively transported by E. coli and both can be used efficiently as a sole carbon source under oxidative conditions (11). The ability to utilize these diacids as a sole carbon source when alternative electron acceptors become available may have been an evolutionary advantage.

TABLE 1

Comparison of malate production by natural and metabolically engineered microorganisms

| Microorganism | Medium/condition | Titer (g liter$^{-1}$) | Yield (mol mol$^{-1}$) | Productivity (g liter-1 h$^{-1}$) | Reference |
|---|---|---|---|---|---|
| Natural malate producers | | | | | |
| Aspergillus flavus | Glucose (120 g liter$^{-1}$) in mineral salts medium; 90 g liter$^{-1}$ CaCO3, microaerobic, 25° C., pH 7-pH 5 | 113 | 1.26 | 0.59 | 1 |
| Zygosaccharomyces rouxii | Glucose (300 g liter$^{-1}$) with 5 g liter$^{-1}$ YE, 10 g liter$^{-1}$ peptone, 5 g liter$^{-1}$ glutamate; microaerobic, 25° C., pH 5 | 75 | 0.52 | 0.54 | 24 |
| Engineered strains | | | | | |
| E. coli WGS-10 (p104ManPck) | Glucose (20 g liter$^{-1}$) in mineral salts medium; aerobic batch, 37° C., pH 6.7 | 9.25 | 0.56 | 0.74 | 16 |
| Saccharomyces cerevisiae | Glucose (188 g liter$^{-1}$) in mineral salts medium with 150 g liter$^{-1}$ CaCO$_3$; aerobic flask, 30° C., pH 6 | 59 | 0.42 | 0.19 | 27 |
| Escherichia coli XZ658 | Glucose (50 g liter$^{-1}$) in mineral salts medium with 100 mM KHCO$_3$; anaerobic batch, 37° C., pH 7 | 22 | 1.0 | 0.15 | This study |
| Escherichia coli XZ658 | Glucose (50 g liter$^{-1}$) in mineral salts medium with 100 mM KHCO$_3$; Two-stage, 37° C., pH 7 | 34 | 1.42 | 0.47 | This study |

TABLE 2

Strains, plasmids and primers used in this study

| | Relevant characteristics | Source or reference |
|---|---|---|
| Strains | | |
| KJ060 | E. coli ATCC 8739 ($\Delta$ldhA, $\Delta$ackA, $\Delta$adhE, $\Delta$pflB) | 11 |
| XZ273 | KJ060, $\Delta$fumB | This study |
| XZ276 | XZ273, $\Delta$fumAC | This study |
| XZ277 | XZ276, sequential subculture to improve growth | This study |
| XZ278 | XZ277, $\Delta$aspA | This study |
| XZ280 | XZ277, $\Delta$aspC | This study |
| XZ282 | XZ277, $\Delta$aceA | This study |
| X2372 | KJ060, $\Delta$frdBC | This study |
| KJ073 | KJ060, $\Delta$mgsA, $\Delta$poxB | 11 |
| XZ316 | KJ073, $\Delta$frdBC | This study |
| XZ347 | XZ316, $\Delta$sfcA | This study |
| XZ654 | XZ347, $\Delta$maeB | This study |
| XZ656 | XZ654, $\Delta$fumB | This study |
| XZ658 | XZ656, $\Delta$fumAC | This study |
| XW009 | XZ 658, $\Delta$pykF | This study |
| XW036 | XZ658, $\Delta$pykA | This study |

TABLE 2-continued

Strains, plasmids and primers used in this study

| | Relevant characteristics | Source or reference |
|---|---|---|
| Plasmids | | |
| pCR2.1-TOPO | bla, kan; Cloning vector | Invitrogen |
| pLOI4162 | bla, cat sacB cassette | 12 |
| fumB deletion | | |
| pLOI14743 | bla kan; fumB (PCR) from E. coli cloned into pCR2.1-TOPO vector | This study |
| pLOI4744 | cat-sacB cassette cloned into fumB of pLOI4743 | This study |
| pLOI4745 | PacI digestion of pLOI4744, and self-ligated | This study |
| fumAC deletion | | |
| pLOI4234 | bla kan; fumAC (PCR) from E. coli cloned into pCR2.1-TOPO vector | This study |
| pLOI4235 | cat-sacB cassette cloned into fumAC of pLOI4234 | This study |
| pLOI4246 | bla kan; manA'-fumA-fumC-tus' (PCR) from E. coli cloned into pCR2.1-TOPO vector | This study |
| pLOI4247 | PCR fragment amplified from pLOI4246 (using fumA-5/fumC-3), kinase treated, and then self-ligated | This study |
| aceA deletion | | |
| pLOI4271 | bla kan; aceA (PCR) from E. coli cloned into PCR2.1-TOPO vector | This study |
| pLOI4272 | cat-sacB cassette cloned into aceA of pLOI4271 | This study |
| pLOI4273 | PCR fragment amplified from pLOI4271 (using aceA-1/aceA-2), kinase treated, and then self-ligated | This study |
| aspA deletion | | |
| pLOI4277 | bla kan; aspA (PCR) from E. coli cloned into PCR2.1-TOPO vector | This study |
| pLOI4278 | cat-sacB cassette cloned into aspA of pLOI4277 | This study |
| pLOI4279 | PCR fragment amplified from pLOI4277 (using aspA-1/aspA-2), kinase treated, and then self-ligated | This study |
| aspC deletion | | |
| pLOI4280 | bla kan; aspC (PCR) from E. coli cloned into PCR2.1-TOPO vector | This study |
| pLOI4281 | cat-sacB cassette cloned into aspC of pLOI4280 | This study |
| pLOI4282 | PCR fragment amplified from pLOI4280 (using aspC-1/aspC-2), kinase treated, and then self-ligated | This study |
| frdBC deletion | | |
| pLOI4243 | btu kan; frd (PCR) from E. coli cloned into PCR2.1-TOPO vector | This study |
| pLOI4244A | cat-sacB cassette cloned into frdBC of pLOI4243 | This study |
| pLOI4244 | Pad digestion of pLOI4244A, and self-ligated | This study |
| sfcA deletion | | |
| pLOI4283 | bla kan; sfcA (PCR) from E. coli cloned into PCR2.1-TOPO vector | This study |
| pLOI4284 | cat-sacB cassette cloned into sfcA of pLOI4283 | This study |
| pLOI4285 | Pad digestion of pLOI4284, and self-ligated | This study |
| maeB deletion | | |
| pLOI4728 | bla kan; maeB (PCR) from E. coli cloned into PCR2.1-TOPO vector | This study |
| pLOI4729 | cat-sacB cassette cloned into maeB of pLOI4728 | This study |
| pLOI4730 | PacI digestion of pLOI4729, and self-ligated | This study |
| pykF deletion | | |
| pLOI4701 | bla kan; pykF (PCR) from E. coli cloned into PCR2.1-TOPO vector | This study |
| pLOI4702 | cat-sueR cassette cloned into pykF of pLOI4701 | This study |
| pLOI5124 | PacI1 digestion of pLOI4702, and self-ligated | This study |

TABLE 2-continued

Strains, plasmids and primers used in this study

| | Relevant characteristics | Source or reference |
|---|---|---|
| pykA deletion | | |
| pLOI5147 | bla kan; pykA (PCR) from *E. coli* cloned into PCR2.1-TOPO vector | This study |
| pLOI5150 | cat-sacB cassette cloned into pykA of pLOI5147 | This study |
| pLOI5153 | PacI digestion of pLOI5150, and self-ligated | This study |
| Primers | | |
| fumB deletion | | |
| fumB-up2 | GCCTATGCCATTGTTCTGCT (SEQ ID NO: 1) | This study |
| fumB-down2 | GGGACTTTCGCGTAGGTGTA (SEQ ID NO: 2) | |
| fumB-1 | CTTCCAGCAAATCGTCAACA (SEQ ID NO: 3) | |
| fumB-2 | GGGAAAGGTGCCTGGTAGAT (SEQ ID NO: 4) | |
| fumAC deletion | | |
| fumA-up | CCTGAATGGAGAGTGGCTGT (SEQ ID NO: 5) | This study |
| fumC-down | GGCTGATCACCCTTAATGCTT (SEQ ID NO: 6) | |
| fumA-5 | TGAGTGGAAAAGGAGCCTGA (SEQ ID NO: 7) | |
| fumC-3 | GTACGGCCAGAACAGATGGT (SEQ ID NO: 8) | |
| aceA deletion | | |
| aceA-up | AACGCACCGAAGAAGGTATG (SEQ ID NO: 9) | This study |
| aceA-down | CACTTCGAGGAATCGACCAT (SEQ ID NO: 10) | |
| aceA-1 | ACCGGCTCCACTGAAGAAT (SEQ ID NO: 11) | |
| aceA-2 | GCGGTTGAGTCCACTCTTTC (SEQ ID NO: 12) | |
| aspA deletion | | |
| aspA-up | TAACCAGCGCAAAGGTTTCT (SEQ ID NO: 13) | This study |
| aspA-down | GCAGCAGCTTTTCTGTCTGA (SEQ ID NO: 14) | |
| aspA-1 | CGGCTTACAAAGCAAAACG (SEQ ID NO: 15) | |
| aspA-2 | CTTCCCTGGTACCCAACAGA (SEQ ID NO: 16) | |
| aspC deletion | | |
| aspC-up | TCCATCGCTTACACCAAATC (SEQ ID NO: 17) | This study |
| aspC-down | TGGGGGATGACGTGATATTT (SEQ ID NO: 18) | |
| aspC-1 | AGATAACATGGCTCCGCTGT (SEQ ID NO: 19) | |
| aspC-2 | AGGAGCGGCGGTAATGTTC (SEQ ID NO: 20) | |
| frdBC deletion | | |
| frdB-up | TGCAGAAAACCATCGACAAG (SEQ ID NO: 21) | This study |
| frdC-down | CACCAATCAG CGTGACAACT (SEQ ID NO: 22) | |
| XZ-frdC-1 | GCCACCATCGTAATCCTGTT (SEQ ID NO: 23) | |
| XZ-frdB-2 | ATAGCGCACCACCTCAATTT (SEQ ID NO: 24) | |
| sfcA deletion | | |
| sfcA-up | CTATGCTTGATCGGCAACCT (SEQ ID NO: 25) | This study |
| sfcA-down | ACGATCGCCTGGTTTTAATG (SEQ ID NO: 26) | |
| sfcA-1 | TACCGCCGTACCTCCATCTA (SEQ ID NO: 27) | |
| sfcA-2 | CGTAAGGGATATAAAGCGAACG (SEQ ID NO: 28) | |
| maeB deletion | | |
| maeB-up | GCATCCTGGGGATGATAATG (SEQ ID NO: 29) | This study |
| maeB-down | TTTCTTCGCCAGTTCCTCAC (SEQ ID NO: 30) | |
| maeB-1 | AACCCAACCGCTGTAATTTTT (SEQ ID NO: 31) | |
| maeB-2 | CTGGAACTGGAAATTCATGG (SEQ ID NO: 32) | |
| pykF deletion | | |
| pykF-up | TGCGCAAACAGTGAAGTTTT (SEQ ID NO: 33) | This study |
| pykF-down | CCTGCCAGCAGAGTAGAACC (SEQ ID NO: 34) | |
| pykF-1 | GGTACCGAGCGGCACTACTA (SEQ ID NO: 35) | |
| pykF-2 | TCCGATGGTGCAAACAATTT (SEQ ID NO: 36) | |

TABLE 2-continued

Strains, plasmids and primers used in this study

| | Relevant characteristics | Source or reference |
|---|---|---|
| | pykA deletion | |
| pykA-up | AAAATCGCCTTTTTCGGATT (SEQ ID NO: 37) | This study |
| pykA-down | ACCGCTGTTTCCGATTTATG (SEQ ID NO: 38) | |
| pykA-1 | GTACGTTGCCGGAT (SEQ ID NO: 39) | |
| pykA-2 | GTAATACTCCGTTGACTGAAACAACC (SEQ ID NO: 40) | |

TABLE 3

Effects of gene deletions on succinate production

| Strain | Genetic modification | Time (days) | Cell mass (g liter$^{-1}$) | Fermentation products (mM) $^{a, b}$ | | | | |
|---|---|---|---|---|---|---|---|---|
| | | | | Mal | Suc | Pyr | Ace | For |
| KJ060 | ATCC 8739, ΔldhA, ΔackA, ΔadhE, ΔpflB | 2 | 1.9 | — | 127 | — | 31 | 2 |
| XZ273 | KJ060, ΔfumB | 4 | 0.6 | — | 47 | — | 10 | — |
| XZ276 | XZ273, ΔfumAC | 6 | 0.47 | 27 | 4 | 4 | 15 | — |
| XZ276 | XZ273, ΔfumAC | 9 | 1.1 | — | 56 | — | 45 | — |
| XZ277 $^c$ | XZ276, sequential subculture | 2 | 1.07 | 1 | 71 | — | 35 | — |
| XZ278 | XZ277, ΔaspA | 2 | 1.37 | 2 | 82 | — | 43 | — |
| XZ280 | XZ277, ΔaspC | 2 | 1.17 | 1 | 78 | — | 31 | — |
| XZ282 | XZ277, ΔaceA | 2 | 1.43 | 1 | 97 | — | 46 | — |

$^a$ Fermentations were carried out in NBS mineral salts medium with 2% glucose and 100 mM potassium bicarbonate (37° C., pH 7.0, 150 rpm).
$^b$ Abbreviations: Mal, malate; Suc, succinate; Pyr, pyruvate; Ace, acetate; For, formate.
$^c$ Sequential subculture (improvement in growth).

TABLE 4

Effects of gene deletions on malate production

| Strain | Genetic modifications | Time Days | Cell mass (g/L) | Gluc used (mM) | Mal yield$^a$ | Fermentation products (mM) | | | | |
|---|---|---|---|---|---|---|---|---|---|---|
| | | | | | | Mal | Fum | Suc | Pyr | Lac | Ace |
| KJ060$^b$ | ATCC 8739, ΔldhA, ΔackA, ΔadhE, ΔpflB | 2 | 1.9 | 277 | 0 | — | — | 291 | 2 | — | 125 |
| XZ372$^b$ | KJ060, ΔfrdBC | 6 | 0.5 | 72 | 0.53 ± 0.08 | 38 ± 6 | 1 | 9 | 16 | — | 40 |
| KJ073$^b$ | KJ060, ΔmgsA, ΔpoxB | 2 | 2.2 | 277 | 0 | — | — | 339 | 6 | — | 115 |
| XZ316$^b$ | KJ073, ΔfrdBC | 6 | 0.44 | 55 | 0.44 ± 0.06 | 24 ± 3 | 1 | 5 | 74 | — | 5 |
| XZ347$^b$ | XZ316, sfcA | 6 | 0.53 | 99 | 0.71 ± 0.10 | 70 ± 11 | 1 | 9 | 51 | — | 15 |
| XZ654$^b$ | XZ347, maeB | 6 | 0.33 | 45 | 0.89 ± 0.11 | 40 ± 5 | 1 | 4 | 3 | 2 | 10 |
| XZ658$^b$ | XZ654, ΔfumB, ΔfumAC | 6 | 0.75 | 163 | 1.0 ± 0.13 | 163 ± 22 | 1 | 4 | 13 | 78 | 6 |
| XZ658$^c$ | XZ654, ΔfumB, ΔfumAC | 6 | 0.85 | 216 | 0.91 ± 0.06 | 197 ± 13 | — | 14 | 50 | 156 | 15 |
| XW009$^b$ | XZ658, ΔpykF | 6 | 0.46 | 85 | 1.3 ± 0.07 | 111 ± 15 | — | 2 | 21 | 5 | 11 |
| XW036$^b$ | XZ658, ΔpykA | 6 | 0.42 | 74 | 1.1 ± 0.04 | 84 ± 7 | — | 3 | 33 | 5 | 11 |
| XZ658$^d$ | XZ654, ΔfumB, ΔfumAC | 3 | 2.5 | 182 | 1.42 | 253 | — | 10 | — | 12 | 8 |

$^a$Yield was calculated as mol malate produced per mol glucose consumed.
$^b$Fermentations were carried out in a 500 ml fleaker with 300 ml NBS mineral salts medium with 5% glucose, 10 mM acetate, and 100 mM potassium bicarbonate (37° C., pH 7.0, 150 rpm). Acetate was added to improve cell growth. Abbreviations: Mal, malate; Fum, fumarate; Suc, succinate; Pyr, pyruvate; Lac, D-lactate; Ace, acetate.
$^c$Fermentation supplemented with 57 mM pyruvate.
$^d$XZ658 was tested with two-stage process (aerobic cell growth and anaerobic malate production).

TABLE 5

Ruminant bacterial cells

*Fibrobacter (Bacteroides) succinogenes*
*Ruminococcus albus*
*Ruminococcus flavefaciens*
*Butyrivibrio fibrisolvens*
*Clostridium lochheadii*
*Streptococcus bovis*
*Ruminobacter (Bacteroides) amylophilus*
*Prevotella (Bacteroides) ruminocola*
*Succinimonas amylolytica*
*Selenomonas ruminantium*
*Lachnospira multiparus*
*Succinivibrio dextrinosolvens*
*Methanobrevibacter ruminantium*
*Methanosarcina barkeri*
*Treponema bryantii*
*Megasphaera elsdenii*
*Lactobacillus* sp.
*Anaerovibrio lipolytica*
*Eubacterium ruminantium*
*Oxalobacter formigenes*
*Wolinella succinogenes*

TABLE 6

| Culture | Strain Designations | Deposit Date |
|---|---|---|
| XZ372 | NRRL B-50411 | Aug. 24, 2010 |
| XZ316 | NRRL B-50412 | Aug. 24, 2010 |
| XZ347 | NRRL B-50413 | Aug. 24, 2010 |
| XZ654 | NRRL B-50414 | Aug. 24, 2010 |
| XZ658 | NRRL B-50415 | Aug. 24, 2010 |
| XW009 | NRRL B-50416 | Aug. 24, 2010 |
| XW036 | NRRL B-50417 | Aug. 24, 2010 |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Battat, E., Y. Peleg, A. Bercovitz, J. S. Rokem, and I. Goldberg. 1991. Optimization of L-malic acid production by *Aspergillus flavus* in a stirred fermentor. Biotechnol Bioeng 37:1108-16.

2. Bressler, E., O. Pines, I. Goldberg, and S. Braun. 2002. Conversion of fumaric acid to L-malic by sol-gel immobilized *Saccharomyces cerevisiae* in a supported liquid membrane bioreactor. Biotechnol Prog 18:445-50.

3. Causey, T. B., K. T. Shanmugam, L. P. Yomano, and L. O. Ingram. 2004. Engineering *Escherichia coli* for efficient conversion of glucose to pyruvate. Proc Natl Acad Sci USA 101:2235-40.

4. Causey, T. B., S. Zhou, K. T. Shanmugam, and L. O. Ingram. 2003. Engineering the metabolism of *Escherichia coli* W3110 for the conversion of sugar to redox-neutral and oxidized products: homoacetate production. Proc Natl Acad Sci USA 100:825-32.

5. Geiser, D. M., J. I. Pitt, and J. W. Taylor. 1998. Cryptic speciation and recombination in the aflatoxin-producing fungus *Aspergillus flavus*. Proc Natl Acad Sci USA 95:388-93.

6. Giorno, L., E. Drioli, G. Carvoli, A. Cassano, and L. Donato. 2001. Study of an enzyme membrane reactor with immobilized fumarase for production of L-malic acid. Biotechnol Bioeng 72:77-84.

7. Goldberg, I., J. S. Rokem, and 0. Pines. 2006. Organic acids: old metabolites, new themes. J Chem Technol Biot 81:1601-1611.

8. Grabar, T. B., S. Zhou, K. T. Shanmugam, L. P. Yomano, and L. O. Ingram. 2006. Methylglyoxal bypass identified as source of chiral contamination in 1(+) and d(-)-lactate fermentations by recombinant *Escherichia coli*. Biotechnol Lett 28:1527-35.

9. Henry, C. S., M. D. Jankowski, L. J. Broadbelt, and V. Hatzimanikatis. 2006. Genome-scale thermodynamic analysis of *Escherichia coli* metabolism. Biophys J 90:1453-61.

10. Howell, B. F., S. McCune, and R. Schaffer. 1979. Lactate-to-pyruvate or pyruvate-to-lactate assay for lactate dehydrogenase: a re-examination. Clin Chem 25:269-72.

11. Janausch, I. G., E. Zientz, Q. H. Tran, A. Kroger, and G. Unden. 2002. C4-dicarboxylate carriers and sensors in bacteria. Biochim Biophys Acta 1553:39-56.

12. Jantama, K., M. J. Haupt, S. A. Svoronos, X. Zhang, J. C. Moore, K. T. Shanmugam, and L. O. Ingram. 2008. Combining metabolic engineering and metabolic evolution to develop nonrecombinant strains of *Escherichia coli* C that produce succinate and malate. Biotechnol Bioeng 99:1140-53.

13. Jantama, K., X. Zhang, J. C. Moore, K. T. Shanmugam, S. A. Svoronos, and L. O. Ingram. 2008. Eliminating side products and increasing succinate yields in engineered strains of *Escherichia coli* C. Biotechnol Bioeng 101:881-93.

14. Kao, K. C., L. M. Tran, and J. C. Liao. 2005. A global regulatory role of gluconeogenic genes in *Escherichia coli* revealed by transcriptome network analysis. J Biol Chem 280:36079-87.

15. Karp, P. D., 1. M. Keseler, A. Shearer, M. Latendresse, M. Krummenacker, S. M. Paley, I. Paulsen, J. Collado-Vides, S. Gama-Castro, M. Peralta-Gil, A. Santos-Zavaleta, M. I. Penaloza-Spinola, C. Bonavides-Martinez, and J. Ingraham. 2007. Multidimensional annotation of the *Escherichia coli* K-12 genome. Nucleic Acids Res 35:7577-90.

16. Kawagoe, M., K. Hyakumura, S. I. Suye, K. Mild, and K. Naoe. 1997. Application of bubble column fermenters to submerged culture of *Schizophyllum commune* for production of L-malic acid. J Ferment Bioeng 84:333-336.

17. Moon, S. Y., S. H. Hong, T. Y. Kim, and S. Y. Lee. 2008. Metabolic engineering of *Escherichia coli* for the production of malic acid. Biochem Eng J 40:312-320.

18. Peleg, Y., J. S. Rokem, and I. Goldberg. 1990. A simple plate-assay for the screening of L-malic acid producing microorganisms. FEMS Microbiol Lett 55:233-6.

19. Pines, O., S. Even-Ram, N. Elnathan, E. Battat, O. Aharonov, D. Gibson, and I. Goldberg. 1996. The cytosolic pathway of L-malic acid synthesis in *Saccharomyces cerevisiae*: the role of fumarase. Appl Microbiol Biotechnol 46:393-9.

20. Pines, O., S. Shemesh, E. Battat, and I. Goldberg. 1997. Overexpression of cytosolic malate dehydrogenase (MDH2) causes overproduction of specific organic acids in *Saccharomyces cerevisiae*. Appl Microbiol Biotechnol 48:248-55.

21. Presecki, A. V., and D. Vasic-Racki. 2005. Production of L-malic acid by permeabilized cells of commercial *Saccharomyces* sp. strains. Biotechnol Lett 27:1835-9.

22. Roa Engel, C. A., A. J. Straathof, T. W. Zijlmans, W. M. van Gulik, and L. A. van der Wielen. 2008. Fumaric acid production by fermentation. Appl Microbiol Biotechnol 78:379-89.

23. Rosenberg, M., H. Mikova, and L. Kristofikova. 1999, Formation of L-malic acid by yeasts of the genus *Dipodascus*. Lett Appl Microbiol 29:221-3.

24. Stols, L., and M. I. Donnelly. 1997. Production of succinic acid through overexpression of NAD(+)-dependent malic enzyme in an *Escherichia coli* mutant. Appl Environ Microbiol 63:2695-701.

25. Taing, O., and K. Taing. 2007. Production of malic and succinic acids by sugar-tolerant yeast *Zygosaccharomyces rouxii*. Eur Food Res Technol 224:343-347.

26. Tseng, C. P., C. C. Yu, H. H. Lin, C. Y. Chang, and J. T. Kuo. 2001. Oxygen- and growth rate-dependent regulation of *Escherichia coli* fumarase (FumA, FumB, and FumC) activity. J Bacteriol 183:461-7.

27. Werpy, T., and G. Petersen. 2004. Top value added chemicals from biomass. Washington, DC. US Department of Energy. web site: www1.eere.energy.gov/biomass/pdfs/35523.pdf.

28. Zelle, R. M., E. de Hulster, W. A. van Winden, P. de Waard, C. Dijkema, A. A. Winkler, J. M. Geertman, J. P. van Dijken, J. T. Pronk, and A. J. van Maris. 2008. Malic acid production by *Saccharomyces cerevisiae*: engineering of pyruvate carboxylation, oxaloacetate reduction, and malate export. Appl Environ Microbiol 74:2766-77.

29. Zhang, X., K. Jantama, J. C. Moore, L. R. Jarboe, K. T. Shanmugam, and L. O. Ingram. 2009. Metabolic evolution of energy-conserving pathways for succinate production in *Escherichia coli*. Proc Natl Acad Sci USA 106:20180-5.

30. Zhang, X., K. Jantama, J. C. Moore, K. T. Shanmugam, and L. O. Ingram. 2007. Production of L-alanine by metabolically engineered *Escherichia coli*. Appl Microbiol Biotechnol 77:355-66.

31. Zhang, X., K. Jantama, K. T. Shanmugam, and L. O. Ingram. 2009. Reengineering *Escherichia coli* for Succinate Production in Mineral Salts Medium. Appl Environ Microbiol 75:7807-13.

32. Babitzke, P., Romeo, T. (2007) "CsrB sRNA family: sequestration of RNA-binding regulatory proteins" *Curr Opin Microbiol* 10:156-163.

33. Jantama, K., Haupt, M. J., Svoronos, S. A., Zhang, X., Moore, J. C., Shanmugam, K. T., Ingram, L. O. (2008a) "Combining metabolic engineering and metabolic evolution to develop nonrecombinant strains of *E. coli* C that produce succinate and malate" *Biotech Bioeng* 99:1140-1153.

34. Jantama, K., Zhang, X., Moore, J. C., Shanmugam, K. T., Svoronos, S. A., Ingram, L. O. (2008b) "Eliminating side products and increasing succinate yields in engineered strains of *Escherichia coli* C" *Biotechnol Bioeng* 101:881-893.

35. Jojima, T., Omumasaba, C. A., Inui, M., and Yukawa, H. (2010) Sugar transporters in efficient utilization of mixed sugar substrates: current knowledge and outlook. *Appl Microbiol Biotechnol* 85: 471-480.

36. Pernestig, A. K., Georgellis, D., Romeo, T., Suzuki, K., Tomenius, H., Normakr, S., Melefors, O. (2003) "The *Escherichia coli* BarA-UvrY two-component system is needed for efficient switching between glycolytic and gluconeogenic carbon sources" *J Bacteriol* 185:843-853.

37. Saier, M. H. Jr, and Ramseier, T. M. (1996) "The catabolite repressor/activator (Cra) protein of enteric bacteria" *J Bacteriol* 178:3411-3417.

38. Suzuki, K., Wang, X., Weilbacher, T., Pernestig, A. K., Melefors, O., Georgellis, D., Babitzke, P., Romeo, T. (2002) "Regulatory circuitry of the CsrA/CsrB and BarA/UvrY systems of *Escherichia coli*" *J Bacteriol* 184:5130-5140.

39. Yi, J., Draths, K. M., Li, K., Frost, J. W. (2003) "Altered glucose transport and shikimate pathway product yields in *E. coli*" *Biotechnol Prog* 19:1450-1459.

We claim:

1. An isolated bacterial cell, said bacterial cell lacking fumarate reductase (FRD) activity and having increased levels of phosphoenol pyruvate carboxykinase (PCK) activity as compared to endogenous PCK activity of the parental bacterial strain, wherein FRD activity is inactivated by genetic modification of said bacterial cell via genetic modification of a gene selected from frdA, frdB, fdrC, frdD, frdAB, frdAC, frdAD, frdBC, frdBD, frdCD, frdABC, frdCBD, frdACD, frdABD, frdABCD or combinations thereof and said genetic modification comprises complete or partial deletion of a coding region of the gene, introducing frame shift mutations within the coding region of the gene, insertions of sequences that disrupt the activities of the proteins encoded by the genes, introduction of stop codons in the coding region of the gene or any combination thereof, the bacterial cell further comprising inactivation of genes encoding lactate dehydrogenase (ldhA), alcohol dehydrogenase (adhE), acetate kinase (ackA), and pyruvate-formate lyase (pflB), said inactivation comprises complete or partial deletion of a coding region of the gene, introducing frame shift mutations within the coding region of the gene, insertions of sequences that disrupt the activities of the proteins encoded by the genes, introduction of stop codons in the coding region of the gene or any combination thereof; and said increased levels of PCK activity arising from:

a) replacement of a native promoter sequence either with a constitutive or inducible heterologous promoter operably linked to the endogenous pck gene;
  b) expression of a multicopy plasmid with a native promoter or an exogenous promoter sequence operably linked to a pck gene;
  c) integration of additional copies of the pck gene into the bacterial cell genome; or
  d) replacement of nucleotide G with nucleotide A at position 64 up stream of the endogenous pck gene start codon when the bacterial cell is an *E. coli* cell.

2. The bacterial cell according to claim 1, wherein said bacterial cell is selected from *Escherichia coli, Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocar-

*boglutamicus, Arthrobacter oxydans, Aureobacterium saperdae, Azotobacter indicus, Bacillus licheniformis, Bacillus subtilis, Bacillus amyloliquifaciens, Brevibacterium ammoniagenes, divaricatum, Brevibacterium lactofermentum, Brevibacterium flavum, Brevibacterium globosum, Brevibacterium fuscum, Brevibacterium ketoglutamicum. Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus licheniformis, Bacillus subtilis, Bacillus amyloliquifaciens, Bacillus coagulans, Escherichia freundii, Microbacterium ammoniaphilum, Serratia marcescens, Salmonella typhimurium, Salmonella schottmulleri,* or *Xanthomonas citri.*

3. The bacterial cell according to claim 1, wherein the increased levels of said PCK activity results from replacement of native regulatory sequences of pck gene with altered regulatory sequences of the pck gene that increase pck transcription.

4. The bacterial cell according to claim 1, wherein increased levels of said PCK activity in said bacterial cell result from replacement of the native promoter sequence of pck gene with an exogenous promoter sequence.

5. The bacterial cell according to claim 1, wherein said bacterial cell further comprises one or more genetic modification that disrupts the functioning of the proteins encoded by one or more genes selected from phosphotransferase system (PTS) glucose-specific enzyme IICB component (ptsG), PTS phosphocarrier protein PtsH (ptsH), phosphoenolpyruvate-protein phosphotransferase PtsI (ptsI), PTS glucose-specific enzyme IIA component (crr) and cAMP receptor protein (crp), wherein said genetic modification comprises complete or partial deletions of the coding regions of the genes, introducing frame shift mutations within the coding regions of the genes, insertions of sequences that disrupt the activities of the proteins encoded by the genes, by introducing stop codons in the coding regions of the genes, or any combination thereof.

6. The bacterial cell according to claim 1, further comprising: (a) one or more genetic modifications of said bacterial cell that disrupt the functioning of the proteins encoded by one or more genes selected from ptsG, ptsH, ptsI, crr, and crp, wherein said genetic modification comprises complete or partial deletions of the coding regions of the genes, introducing frame shift mutations within the coding regions of the genes, insertions of sequences that disrupt the activities of the proteins encoded by the genes, by introducing stop codons in the coding regions of the genes, or any combination thereof; and (b) one or more genetic modifications in said bacterial cell that upregulate the expression of one or more genes encoding sugar transporters, wherein said sugar transporter is a member of ATP binding cassette transporters or a member of major facilitator super family, and wherein said genetic modifications that upregulate the expression of genes expressing sugar transporters comprise expressing exogenous genes encoding the sugar transporters under constitutive promoters.

7. The bacterial cell according to claim 6, wherein said sugar transporter is a member of ATP binding cassette transporters.

8. The bacterial cell according to claim 6, wherein said sugar transporter is a member of major facilitator super family.

9. The bacterial cell according to claim 1, further comprising genetic modification of said bacterial cell leading to the inactivation of gene expression in:
a) one or more genes selected from the group consisting of methylglyoxal synthase (mgsA), malic enzyme (sfcA or maeB), fumarase isozyme A (fumA), fumarase isozyme B (fumB), fumarase isozyme C (fumC), and pyruvate oxidase (poxB), wherein said genetic modification comprises complete or partial deletion of the coding regions of the genes, introducing frame shift mutations within the coding region of the genes, insertions of sequences that disrupt the activities of the proteins encoded by the genes, by introducing stop codons in the coding regions of the genes, or any combination thereof.

10. A method of producing malic acid comprising:
a) culturing a bacterial strain according to claim 1 in a carbon source;
b) allowing said bacteria to metabolize said carbon source; and
c) isolating malic acid.

11. The method according to claim 10, wherein said bacterial strain is cultured in anaerobic condition, aerobic condition, microaerobic condition or combinations thereof.

* * * * *

UNITED STATES PATENT AND TRADEMARK OFFICE
CERTIFICATE OF CORRECTION

PATENT NO. : 9,187,772 B2
APPLICATION NO. : 13/819773
DATED : November 17, 2015
INVENTOR(S) : Xueli Zhang et al.

It is certified that error appears in the above-identified patent and that said Letters Patent is hereby corrected as shown below:

IN THE SPECIFICATION

Column 2,
Line 58, "furA," should read --fumA,--.

Column 4,
Line 22, "DNA as well" should read --DNA, as well--.
Line 22, "derived form" should read --derived from--.

Column 5,
Line 34, "Proteus retigeri," should read --Proteus rettgeri,--.

Column 11,
Line 1, "gene err" should read --gene crr--.
Line 25, "and gallR." should read --and galR.--.

Column 20,
Line 36, "and aced" should read --and aceA--.

Column 22,
Line 33, "0.56 mol" should read --0.56 mol mol$^{-1}$,--.

Column 25,
Line 46, "pLOI4243    btu kan;" should read --pLOI4243    bla kan;--.
Line 49, "pLOI4244    Pad"     should read --pLOI4244    PacI--.
Line 55, "pLOI4285    Pad"     should read --pLOI4285    PacI--.
Line 65, "pLOI4702    cat-sueR" should read --pLOI4702    cat-sacB--.
Line 66, "pLOI5124    PacI1"   should read --pLOI5124    PacI--.

Signed and Sealed this
Fifth Day of April, 2016

Michelle K. Lee
*Director of the United States Patent and Trademark Office*

CERTIFICATE OF CORRECTION (continued)
U.S. Pat. No. 9,187,772 B2

IN THE SPECIFICATION

<u>Column 32,</u>
Line 42, "K. Mild," should read --K. Miki,--.

```
                        SEQUENCE LISTING

<160> NUMBER OF SEQ ID NOS: 40

<210> SEQ ID NO 1
<211> LENGTH: 20
<212> TYPE: DNA
<213> ORGANISM: Artificial sequence
<220> FEATURE:
<223> OTHER INFORMATION: fumB-up2 primer

<400> SEQUENCE: 1
gcctatgcca ttgttctgct                                               20

<210> SEQ ID NO 2
<211> LENGTH: 20
<212> TYPE: DNA
<213> ORGANISM: Artificial sequence
<220> FEATURE:
<223> OTHER INFORMATION: fumB-down2 primer

<400> SEQUENCE: 2
gggactttcg cgtaggtgta                                               20

<210> SEQ ID NO 3
<211> LENGTH: 20
<212> TYPE: DNA
<213> ORGANISM: Artificial sequence
<220> FEATURE:
<223> OTHER INFORMATION: fumB-1 primer

<400> SEQUENCE: 3
```

```
cttccagcaa atcgtcaaca                                               20

<210> SEQ ID NO 4
<211> LENGTH: 20
<212> TYPE: DNA
<213> ORGANISM: Artificial sequence
<220> FEATURE:
<223> OTHER INFORMATION: fumB-2 primer

<400> SEQUENCE: 4
gggaaaggtg cctggtagat                                               20

<210> SEQ ID NO 5
<211> LENGTH: 20
<212> TYPE: DNA
<213> ORGANISM: Artificial sequence
<220> FEATURE:
<223> OTHER INFORMATION: fumA-up primer

<400> SEQUENCE: 5
cctgaatgga gagtggctgt                                               20

<210> SEQ ID NO 6
<211> LENGTH: 21
<212> TYPE: DNA
<213> ORGANISM: Artificial sequence
<220> FEATURE:
<223> OTHER INFORMATION: fumC-down primer

<400> SEQUENCE: 6
ggctgatcac ccttaatgct t                                             21

<210> SEQ ID NO 7
<211> LENGTH: 20
<212> TYPE: DNA
<213> ORGANISM: Artificial sequence
<220> FEATURE:
<223> OTHER INFORMATION: fumA-5 primer

<400> SEQUENCE: 7
tgagtggaaa aggagcctga                                               20

<210> SEQ ID NO 8
<211> LENGTH: 20
<212> TYPE: DNA
<213> ORGANISM: Artificial sequence
<220> FEATURE:
<223> OTHER INFORMATION: fumC-3 primer

<400> SEQUENCE: 8
gtacggccag aacagatggt                                               20

<210> SEQ ID NO 9
<211> LENGTH: 20
<212> TYPE: DNA
<213> ORGANISM: Artificial sequence
<220> FEATURE:
<223> OTHER INFORMATION: aceA-up primer

<400> SEQUENCE: 9
aacgcaccga agaaggtatg                                               20

<210> SEQ ID NO 10
<211> LENGTH: 20
<212> TYPE: DNA
<213> ORGANISM: Artificial sequence
```

```
<220> FEATURE:
<223> OTHER INFORMATION: aceA-down primer

<400> SEQUENCE: 10
cacttcgagg aatcgaccat                                                20

<210> SEQ ID NO 11
<211> LENGTH: 19
<212> TYPE: DNA
<213> ORGANISM: Artificial sequence
<220> FEATURE:
<223> OTHER INFORMATION: aceA-1 primer

<400> SEQUENCE: 11
accggctcca ctgaagaat                                                 19

<210> SEQ ID NO 12
<211> LENGTH: 20
<212> TYPE: DNA
<213> ORGANISM: Artificial sequence
<220> FEATURE:
<223> OTHER INFORMATION: aceA-2 primer

<400> SEQUENCE: 12
gcggttgagt ccactctttc                                                20

<210> SEQ ID NO 13
<211> LENGTH: 20
<212> TYPE: DNA
<213> ORGANISM: Artificial sequence
<220> FEATURE:
<223> OTHER INFORMATION: aspA-up primer

<400> SEQUENCE: 13
taaccagcgc aaaggtttct                                                20

<210> SEQ ID NO 14
<211> LENGTH: 20
<212> TYPE: DNA
<213> ORGANISM: Artificial sequence
<220> FEATURE:
<223> OTHER INFORMATION: aspA-down primer

<400> SEQUENCE: 14
gcagcagctt ttctgtctga                                                20

<210> SEQ ID NO 15
<211> LENGTH: 19
<212> TYPE: DNA
<213> ORGANISM: Artificial sequence
<220> FEATURE:
<223> OTHER INFORMATION: aspA-1 primer

<400> SEQUENCE: 15
cggcttacaa agcaaaacg                                                 19

<210> SEQ ID NO 16
<211> LENGTH: 20
<212> TYPE: DNA
<213> ORGANISM: Artificial sequence
<220> FEATURE:
<223> OTHER INFORMATION: aspA-2 primer

<400> SEQUENCE: 16
cttccctggt acccaacaga                                                20
```

<210> SEQ ID NO 17
<211> LENGTH: 20
<212> TYPE: DNA
<213> ORGANISM: Artificial sequence
<220> FEATURE:
<223> OTHER INFORMATION: aspC-up primer

<400> SEQUENCE: 17
tccatcgctt acaccaaatc                                              20

<210> SEQ ID NO 18
<211> LENGTH: 20
<212> TYPE: DNA
<213> ORGANISM: Artificial sequence
<220> FEATURE:
<223> OTHER INFORMATION: aspC-down primer

<400> SEQUENCE: 18
tgggggatga cgtgatattt                                              20

<210> SEQ ID NO 19
<211> LENGTH: 20
<212> TYPE: DNA
<213> ORGANISM: Artificial sequence
<220> FEATURE:
<223> OTHER INFORMATION: aspC-1 primer

<400> SEQUENCE: 19
agataacatg gctccgctgt                                              20

<210> SEQ ID NO 20
<211> LENGTH: 19
<212> TYPE: DNA
<213> ORGANISM: Artificial sequence
<220> FEATURE:
<223> OTHER INFORMATION: aspC-2 primer

<400> SEQUENCE: 20
aggagcggcg gtaatgttc                                               19

<210> SEQ ID NO 21
<211> LENGTH: 20
<212> TYPE: DNA
<213> ORGANISM: Artificial sequence
<220> FEATURE:
<223> OTHER INFORMATION: frdB-up primer

<400> SEQUENCE: 21
tgcagaaaac catcgacaag                                              20

<210> SEQ ID NO 22
<211> LENGTH: 20
<212> TYPE: DNA
<213> ORGANISM: Artificial sequence
<220> FEATURE:
<223> OTHER INFORMATION: frdC-down primer

<400> SEQUENCE: 22
caccaatcag cgtgacaact                                              20

<210> SEQ ID NO 23
<211> LENGTH: 20
<212> TYPE: DNA
<213> ORGANISM: Artificial sequence
<220> FEATURE:
<223> OTHER INFORMATION: XZ-frdC-1 primer

```
<400> SEQUENCE: 23
gccaccatcg taatcctgtt                                                20

<210> SEQ ID NO 24
<211> LENGTH: 20
<212> TYPE: DNA
<213> ORGANISM: Artificial sequence
<220> FEATURE:
<223> OTHER INFORMATION: XZ-frdB-2 primer

<400> SEQUENCE: 24
atagcgcacc acctcaattt                                                20

<210> SEQ ID NO 25
<211> LENGTH: 20
<212> TYPE: DNA
<213> ORGANISM: Artificial sequence
<220> FEATURE:
<223> OTHER INFORMATION: sfcA-up primer

<400> SEQUENCE: 25
ctatgcttga tcggcaacct                                                20

<210> SEQ ID NO 26
<211> LENGTH: 20
<212> TYPE: DNA
<213> ORGANISM: Artificial sequence
<220> FEATURE:
<223> OTHER INFORMATION: sfcA-down primer

<400> SEQUENCE: 26
acgatcgcct ggttttaatg                                                20

<210> SEQ ID NO 27
<211> LENGTH: 20
<212> TYPE: DNA
<213> ORGANISM: Artificial sequence
<220> FEATURE:
<223> OTHER INFORMATION: sfcA-1 primer

<400> SEQUENCE: 27
taccgccgta cctccatcta                                                20

<210> SEQ ID NO 28
<211> LENGTH: 22
<212> TYPE: DNA
<213> ORGANISM: Artificial sequence
<220> FEATURE:
<223> OTHER INFORMATION: sfcA-2 primer

<400> SEQUENCE: 28
cgtaagggat ataaagcgaa cg                                             22

<210> SEQ ID NO 29
<211> LENGTH: 20
<212> TYPE: DNA
<213> ORGANISM: Artificial sequence
<220> FEATURE:
<223> OTHER INFORMATION: maeB-up primer

<400> SEQUENCE: 29
gcatcctggg gatgataatg                                                20

<210> SEQ ID NO 30
```

```
<211> LENGTH: 20
<212> TYPE: DNA
<213> ORGANISM: Artificial sequence
<220> FEATURE:
<223> OTHER INFORMATION: maeB-down primer

<400> SEQUENCE: 30
tttcttcgcc agttcctcac                                              20

<210> SEQ ID NO 31
<211> LENGTH: 21
<212> TYPE: DNA
<213> ORGANISM: Artificial sequence
<220> FEATURE:
<223> OTHER INFORMATION: maeB-1 primer

<400> SEQUENCE: 31
aacccaaccg ctgtaatttt t                                            21

<210> SEQ ID NO 32
<211> LENGTH: 20
<212> TYPE: DNA
<213> ORGANISM: Artificial sequence
<220> FEATURE:
<223> OTHER INFORMATION: maeB-2 primer

<400> SEQUENCE: 32
ctggaactgg aaattcatgg                                              20

<210> SEQ ID NO 33
<211> LENGTH: 20
<212> TYPE: DNA
<213> ORGANISM: Artificial sequence
<220> FEATURE:
<223> OTHER INFORMATION: pykF-up primer

<400> SEQUENCE: 33
tgcgcaaaca gtgaagtttt                                              20

<210> SEQ ID NO 34
<211> LENGTH: 20
<212> TYPE: DNA
<213> ORGANISM: Artificial sequence
<220> FEATURE:
<223> OTHER INFORMATION: pykF-down primer

<400> SEQUENCE: 34
cctgccagca gagtagaacc                                              20

<210> SEQ ID NO 35
<211> LENGTH: 20
<212> TYPE: DNA
<213> ORGANISM: Artificial sequence
<220> FEATURE:
<223> OTHER INFORMATION: pykF-1 primer

<400> SEQUENCE: 35
ggtaccgagc ggcactacta                                              20

<210> SEQ ID NO 36
<211> LENGTH: 20
<212> TYPE: DNA
<213> ORGANISM: Artificial sequence
<220> FEATURE:
<223> OTHER INFORMATION: pykF-2 primer

<400> SEQUENCE: 36
```

```
tccgatggtg caaacaattt                                               20

<210> SEQ ID NO 37
<211> LENGTH: 20
<212> TYPE: DNA
<213> ORGANISM: Artificial sequence
<220> FEATURE:
<223> OTHER INFORMATION: pykA-up primer

<400> SEQUENCE: 37
aaaatcgcct ttttcggatt                                               20

<210> SEQ ID NO 38
<211> LENGTH: 20
<212> TYPE: DNA
<213> ORGANISM: Artificial sequence
<220> FEATURE:
<223> OTHER INFORMATION: pykA-down primer

<400> SEQUENCE: 38
accgctgttt ccgatttatg                                               20

<210> SEQ ID NO 39
<211> LENGTH: 14
<212> TYPE: DNA
<213> ORGANISM: Artificial sequence
<220> FEATURE:
<223> OTHER INFORMATION: pykA-1 primer

<400> SEQUENCE: 39
gtacgttgcc ggat                                                     14

<210> SEQ ID NO 40
<211> LENGTH: 26
<212> TYPE: DNA
<213> ORGANISM: Artificial sequence
<220> FEATURE:
<223> OTHER INFORMATION: pykA-2 primer

<400> SEQUENCE: 40
gtaatactcc gttgactgaa acaacc                                        26
```